(12) United States Patent
Rosenblood

(10) Patent No.: US 10,905,358 B2
(45) Date of Patent: Feb. 2, 2021

(54) POSTURE AND DEEP BREATHING IMPROVEMENT DEVICE, SYSTEM, AND METHOD

(71) Applicant: Kenneth Lawrence Rosenblood, Los Angeles, CA (US)

(72) Inventor: Kenneth Lawrence Rosenblood, Los Angeles, CA (US)

( * ) Notice: Subject to any disclaimer, the term of this patent is extended or adjusted under 35 U.S.C. 154(b) by 0 days.

(21) Appl. No.: 16/851,508

(22) Filed: Apr. 17, 2020

(65) Prior Publication Data

US 2020/0289036 A1    Sep. 17, 2020

Related U.S. Application Data

(60) Continuation-in-part of application No. 16/393,483, filed on Apr. 24, 2019, now Pat. No. 10,660,545, which is a continuation-in-part of application No. 16/055,621, filed on Aug. 6, 2018, now Pat. No. 10,307,083, which is a continuation of application No. 15/914,136, filed on Mar. 7, 2018, now Pat. No. 10,064,572, which is a continuation-in-part of application No. 15/676,137, filed on Aug. 14, 2017, now abandoned, which is a division of application No. 14/918,334, filed on Oct. 20, 2015, now Pat. No. 9,763,603.

(60) Provisional application No. 62/066,800, filed on Oct. 21, 2014.

(51) Int. Cl.
*A61B 5/00*   (2006.01)
*A61B 5/11*   (2006.01)
*A61B 5/103*  (2006.01)

(52) U.S. Cl.
CPC ............ *A61B 5/1116* (2013.01); *A61B 5/103* (2013.01); *A61B 5/486* (2013.01); *A61B 5/4836* (2013.01); *A61B 5/74* (2013.01)

(58) Field of Classification Search
CPC ....... A61B 5/103; A61B 5/1116; A61B 5/486; A61B 5/74
USPC ...................................... 340/573.3
See application file for complete search history.

(56) References Cited

U.S. PATENT DOCUMENTS

2011/0063114 A1 *  3/2011  Ikoyan .............. A61B 5/4561
                                                    340/573.7

* cited by examiner

*Primary Examiner* — Ojiako K Nwugo
(74) *Attorney, Agent, or Firm* — Kevin Schraven; Anooj Patel; Hankin Patent Law, APC

(57) ABSTRACT

A posture and breathing improvement device, system, and method. The method may include performing an activity that is created using the system. The activity may be a breathing, stretching, meditation, strength, or the like, activity. The method may comprise having the user do a breathing and movement activity simultaneously. The method may comprise leading the user though the movement activity by providing a follow the target dynamic graphic. The user's current movements may also be displayed so that the user can correct in real time any deficiencies in performing the activity. After the activity is finished, the system displays to the user how the user did and allows the user to compare this to an optimal earlier created target path.

22 Claims, 38 Drawing Sheets

| DASHBOARD | MY PATH | CHALLENGES | MESSAGES | SETTINGS | Start Me/Mo |

SCHEDULE  ACTIVITIES  PROGRAM  DIARY  TRENDS  MY DAY

< EDIT ACTIVITY

| | |
|---|---|
| Intro Sound | Bell |
| Intro Timer | 4 |
| Intro Message | Type Message Here |
| Outro Sound | Cash Register |
| Total Activity Time | 01:20 (?) |

Breathing Pattern   Remove

| | |
|---|---|
| Number of Breathing Cycles | 4 (?) |
| Inhale Length | 4 (?) |
| Inhale Sound | High Gong |
| Hold after Inhale Length | 7 (?) |
| Hold after Inhale Sound | None |
| Exhale Length | 8 (?) |
| Exhale Sound | Reverberating Gong | ←——4857 |
| Hold after Exhale Length | 1 (?) | ←——4858 |
| Hold after Exhale Sound | None | ←——4859 |

+ Add Tutorial Video ←——4880

POSTURE AND DEEP BREATHING IMPROVEMENT DEVICE, SYSTEM, AND METHOD

CROSS REFERENCE TO RELATED APPLICATIONS

This application is a Continuation in Part of U.S. Non-Provisional patent application Ser. No. 16/393,483, now U.S. Pat. No. 10,660,545, filed on Apr. 24, 2019, which is a Continuation in Part of U.S. Non-Provisional patent application Ser. No. 16/055,621, now U.S. Pat. No. 10,307,083, filed on Aug. 6, 2018, which is a Continuation of U.S. Non-Provisional patent application Ser. No. 15/914,136, now U.S. Pat. No. 10,064,572, filed on Mar. 7, 2018, entitled "POSTURE AND DEEP BREATHING IMPROVEMENT DEVICE, SYSTEM, AND METHOD", which is a Continuation in Part of U.S. Non-Provisional patent application Ser. No. 15/676,137, filed on Aug. 14, 2017, entitled "POSTURE IMPROVEMENT DEVICE, SYSTEM, AND METHOD", which is a Divisional Application of U.S. Non-Provisional patent application Ser. No. 14/918,334, now U.S. Pat. No. 9,763,603, filed on Oct. 20, 2015, entitled "POSTURE IMPROVEMENT DEVICE, SYSTEM, AND METHOD", which claims benefit of U.S. Provisional Patent Application No. 62/066,800 filed on Oct. 21, 2014, entitled "POSTURE IMPROVEMENT DEVICE", the contents of all of which are incorporated herein by this reference as though set forth in their entirety, and to which priority and benefit are claimed.

FIELD OF USE

The present disclosure relates generally to systems for improving posture and deep breathing, and more particularly, to systems that conditions a user to practice improved posture and deep breathing through real-time viewing monitoring of their own posture, warnings, reminders to exercise and stretch programs, and behavioral modification.

BACKGROUND

There is a strong correlation between good posture and good health. Many productive hours are lost each year due to pain and sickness associated with posture-induced health issues. Improved posture has been shown to increase levels of dopamine and testosterone produced by the brain, and research has indicated that correction of postural kyphosis in patients with ADHD may lead to a significant reduction of ADHD symptoms. When people operate with good posture, research indicates that performance regarding mental acuity, self-esteem, and physiological efficiency is improved. Thus, providing insight and a mechanism for improving posture has been a desirable goal for many people as it improves mental performance and overall health.

Breathing, like posture, is also important to health. The way humans breathe can impact their whole body. Breathing helps regulate important bodily functions such as heart rate and blood pressure, as well as reinforcing proper body mechanics that put less stress and strain on the body during movements. Deep breathing is associated with better health. Many people are too busy and too sedentary, which has conditioned many to take only take quick, shallow breaths. Over time, this weakens respiratory muscles and can create tension in the upper body. This can change a person's posture and undermine his/her health. Regular physical activity and sessions of respiratory muscle training can reverse problems caused by shallow breathing.

People inhale and exhale air by active contractions of the respiratory muscles that surround a person's lungs. During inhalation, the diaphragm contracts to create space in the chest cavity for the lungs to expand. The intercostal muscles, located between the ribs, assist the diaphragm by elevating the rib cage to allow more air to be taken into the lungs. Additional muscles around the neck and upper chest assist the intercostals if breathing becomes impaired. These additional muscles, which include the sternocleidomastoid, serratus anterior, pectoralis minor, and scalene, act to increase the speed and quantity of movement of the chest.

Breathing from the chest relies primarily on the additional muscles around the neck and collarbone, rather than relying on the diaphragm. When chest breathing is accompanied by poor posture, many muscles in the upper body lose their ability to properly function. The longer a person sits during the day, the less our body is able to fight the forces of gravity and maintain a strong, stable core. Tight accessory muscles around the chest, in particular the pectoralis minor and scalene, may cause rounded shoulders and improper head posture. This may weaken the back muscles by inhibiting the normal use of latissimus dorsi, middle trapezius, and rhomboids, and quadratus lumborum, which are necessary to maintain proper and upright posture.

There are many benefits to deep breathing, which as providing a sense of calm, reducing stress and anxiety, and lowering blood pressure. Deep breathing is the basis for many meditative and mindfulness practices. Thus, deep breathing is very important to a healthy mind and body.

Although wearable devices may remind the wearer to take deep breaths, none of these devices, before the device of the present disclosure, provide a kinetic display that compares a user's actual breathing to an optimal breathing pattern in a gamification manner. Additionally, breathing devices before the device of the present disclosure are not combined with a posture device, wherein the posture device has a copper coil that provides induction charging and protection from and direction of radio waves.

Therefore, there is a need for a device, system, and method that can improve posture and provide a kinetic display that compares a user's actual breathing to an optimal breathing pattern in a gamification manner. Additionally, what is needed is a posture and/or breathing improvement device that has a copper coil that provides induction charging and protection from and direction of radio waves.

SUMMARY OF EMBODIMENTS

To minimize the limitations in the prior art, and to minimize other limitations that will become apparent upon reading and understanding the present disclosure, the present specification discloses a new and improved device, system, and method for improving posture and deep breathing.

One embodiment may be a method of performing a deep breathing and posture activity, comprising the steps: providing two or more sensor devices; providing a posture improvement software program, comprising a posture improvement system interface and a create an activity interface; associating the two or more sensor devices physically with a user; wherein each of the two or more sensor devices comprise: one or more sensors; a wireless communication device; and a housing; wherein each of the one or more sensors, when the two or more sensor devices are physically associated with the user, monitor a physical position of the user and one or more movements of the user; wherein the posture improvement software program is configured to operate on one or more user devices; wherein the wireless communication device is configured to communicate with the one or more user devices, such that the two or more sensor devices are in communication with the posture improvement software program; displaying the posture improvement system interface to the user on the one or more user devices; creating one or more activity programs via the create an activity interface; wherein the one or more activity programs comprise a breathing component, a movement component, and a recordation of a follow the target; starting at least one of the one or more activity programs; performing by the user the at least one of the one or more activity programs; displaying to the user an activity tracker on the posture improvement system interface; displaying on the activity tracker the recordation of a follow the target, a graphical representation of the breathing component, and a graphical representation of the movement component; wherein the recordation of a follow the target provides the user with two or more graphical representations of two or more targets to follow as the user performs the at least one of the one or more activity programs; and transmitting from each of the two or more sensor devices a plurality of movement data to the posture improvement software program, which is translated into the graphical representation of the movement component that is being displayed on the activity tracker, such that a user receives a plurality of real-time visual feed-back related to the user's conformance to the movement component. The posture improvement software program may schedule the one or more activity programs to be performed by the user. The breathing component and the movement component may be synchronized and are performed simultaneously by the user. In some embodiments, each of the two or more targets are a graphical representation of a ball. The one or more activity programs may be selected from the group of activity programs consisting of one or more of: strength; breathing; stretching; meditation; or combinations thereof. The breathing component comprises one or more cycles of deep breathing that comprise at least an inhale and an exhale. The method may also include the step of displaying on the activity tracker two or more ideal paths, which are representative of two or more paths taken by the two or more targets, and two or more actual paths, which are representative of two or more paths taken by the user performing the at least one of the one or more activity programs, such that a user is provided with feed-back as to how the user did in performing the at least one of the one or more activity programs. The method may also include the steps of providing two or more video cameras that are in communication with the posture improvement software program; and displaying on the posture improvement system interface a live feed from the two or more video cameras as the user performs the at least one of the one or more activity programs.

Another embodiment may be a method of performing a deep breathing and posture activity, comprising the steps of: providing at least one sensor device; providing a posture improvement software program, comprising a posture improvement system interface and a create an activity interface; associating the sensor device physically with a user; wherein the sensor device comprises: one or more sensors; a wireless communication device; and a housing; wherein the one or more sensors, when the sensor device is physically associated with the user, monitor a physical position of the user and one or more movements of the user; wherein the posture improvement software program is configured to operate on one or more user devices; wherein the wireless communication device is configured to communicate with the one or more user devices, such that the one or more sensor devices are in communication with the posture improvement software program; displaying the posture improvement system interface to the user on the one or more user devices; creating one or more activity programs via the create an activity interface; wherein the one or more activity programs comprise a movement component and a recordation of a follow the target; starting at least one of the one or more activity programs; performing by the user the at least one of the one or more activity programs; displaying to the user an activity tracker on the posture improvement system interface; displaying on the activity tracker the recordation of a follow the target and a graphical representation of the movement component; wherein the recordation of a follow the target provides the user with a graphical representation of a target to follow as the user performs the at least one of the one or more activity programs; and transmitting from the sensor device a plurality of movement data to the posture improvement software program, which is translated into the graphical representation of the movement component that is being displayed on the activity tracker, such that a user receives a plurality of real-time visual feed-back related to the user's conformance to the movement component. The one or more activity programs may further comprise a breathing component; wherein the breathing component may be displayed as at least one dynamic graphical representation on the activity tracker (usually on the outer rim). The method may also include the steps of: providing two or more video cameras that are in communication with the posture improvement software program; and displaying on the posture improvement system interface a live feed from the two or more video cameras as the user performs the at least one of the one or more activity programs. The posture improvement software program preferably may schedule the one or more activity programs to be performed by the user. The breathing component and the movement component may be synchronized and may be performed simultaneously by the user. Sometimes the target is a graphical representation of a ball. The one or more activity programs may be selected from the group of activity programs consisting of one or more of: strength; breathing; stretching; meditation; or combinations thereof. The breathing component may comprise one or more cycles of deep breathing that comprise at least an inhale and an exhale. The one or more portions of the one or more cycles of deep breathing may be prompted by one or more sounds. The method may include the steps of displaying on the activity tracker an ideal path, which is representative of a path taken by the target, and an actual path, which is representative of a path taken by the user performing the at least one of the one or more activity programs, such that a user is provided with feed-back as to how the user did in performing the at least one of the one or more activity programs.

Another embodiment may be a method of performing a deep breathing and posture activity, comprising the steps of: providing a sensor device; providing a posture improvement software program, comprising a posture improvement system interface and a create an activity interface; associating the sensor device physically with a user; providing two or more video cameras that are in communication with the posture improvement software program; wherein the sensor device comprises: one or more sensors; a wireless communication device; and a housing; wherein the one or more sensors, when the sensor device is physically associated with the user, monitor a physical position of the user and one or more movements of the user; wherein the posture improvement software program is configured to operate on one or more user devices; wherein the wireless communication device is configured to communicate with the one or more user devices, such that the one or more sensor devices are in communication with the posture improvement software program; displaying the posture improvement system interface to the user on the one or more user devices; creating one or more activity programs via the create an activity interface; wherein the one or more activity programs comprise a movement component, a breathing component, and a recordation of a follow the target; starting at least one of the one or more activity programs; performing by the user the at least one of the one or more activity programs; displaying to the user an activity tracker on the posture improvement system interface; displaying on the activity tracker the recordation of a follow the target, a graphical representation of the breathing component, and a graphical representation of the movement component; wherein the recordation of a follow the target provides the user with a graphical representation of a target to follow as the user performs the at least one of the one or more activity programs; and transmitting from the sensor device a plurality of movement data to the posture improvement software program, which is translated into the graphical representation of the movement component that is being displayed on the activity tracker, such that a user receives a plurality of real-time visual feed-back related to the user's conformance to the movement component; displaying on the posture improvement system interface, a live feed from the two or more video cameras as the user performs the at least one of the one or more activity programs; displaying, after a conclusion of the at least one of the one or more activity programs, on the activity tracker, an ideal path, which is representative of a path taken by the target, and an actual path, which is representative of a path taken by the user performing the at least one of the one or more activity programs, such that a user is provided with feed-back as to how the user did in performing the at least one of the one or more activity programs. The breathing component and the movement component may be synchronized and may be performed simultaneously by the user. The one or more activity programs may be selected from the group of activity programs consisting of one or more of: strength; breathing; stretching; meditation; and/or combinations thereof. The at least one of the two or more cameras is configured to show a profile of the user.

These, as well as other components, steps, features, objects, benefits, and advantages, will now become clear from a review of the following detailed description of illustrative embodiments, of the accompanying drawings, and of the claims.

BRIEF DESCRIPTION OF THE ILLUSTRATIVE EMBODIMENTS

The drawings show illustrative embodiments, but do not depict all embodiments. Other embodiments may be used in addition to or instead of the illustrative embodiments. Details that may be apparent or unnecessary may be omitted for the purpose of saving space or for more effective illustrations. Some embodiments may be practiced with additional components or steps and/or without some or all components or steps provided in the illustrations. When different drawings contain the same numeral, that numeral refers to the same or similar components or steps.

Figure 4A:
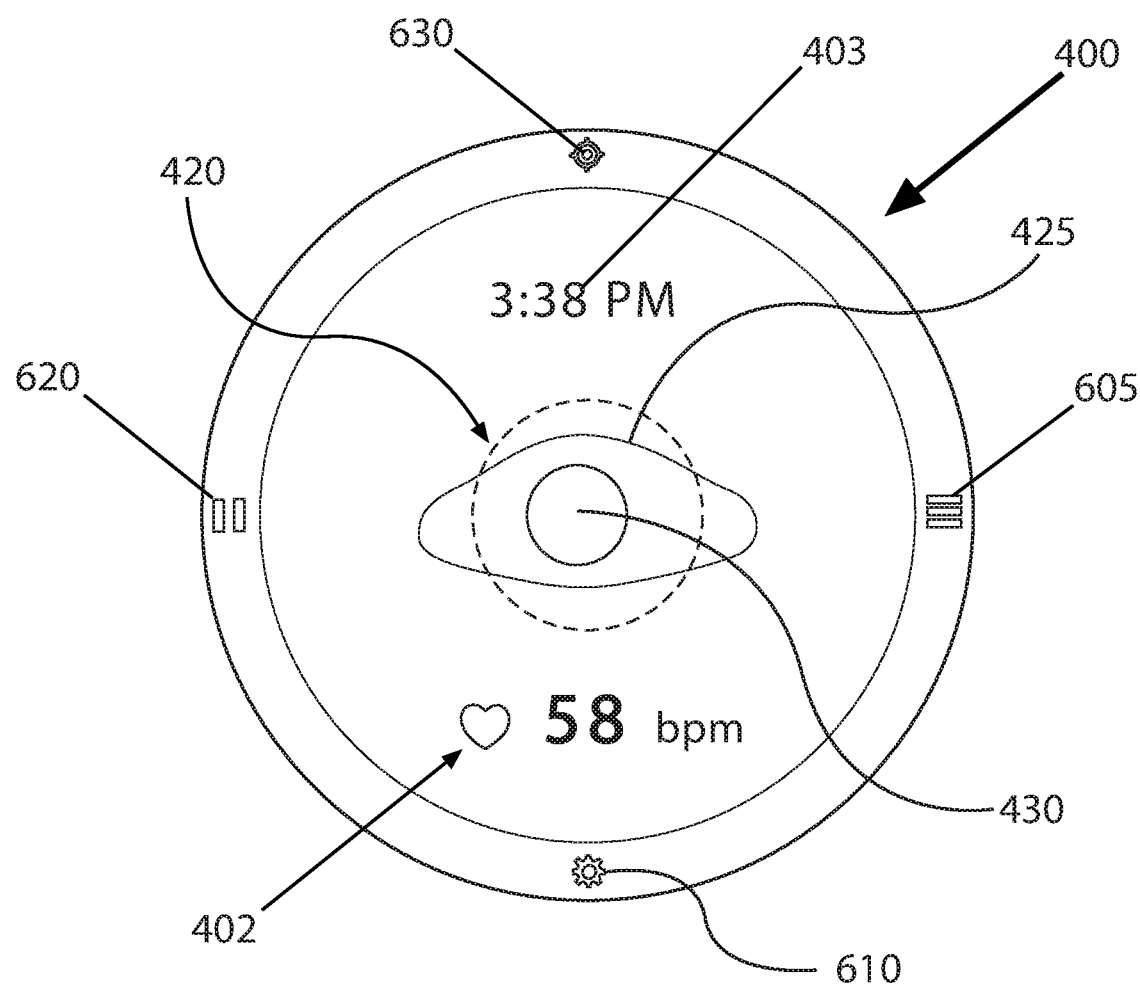
Figure 4B:
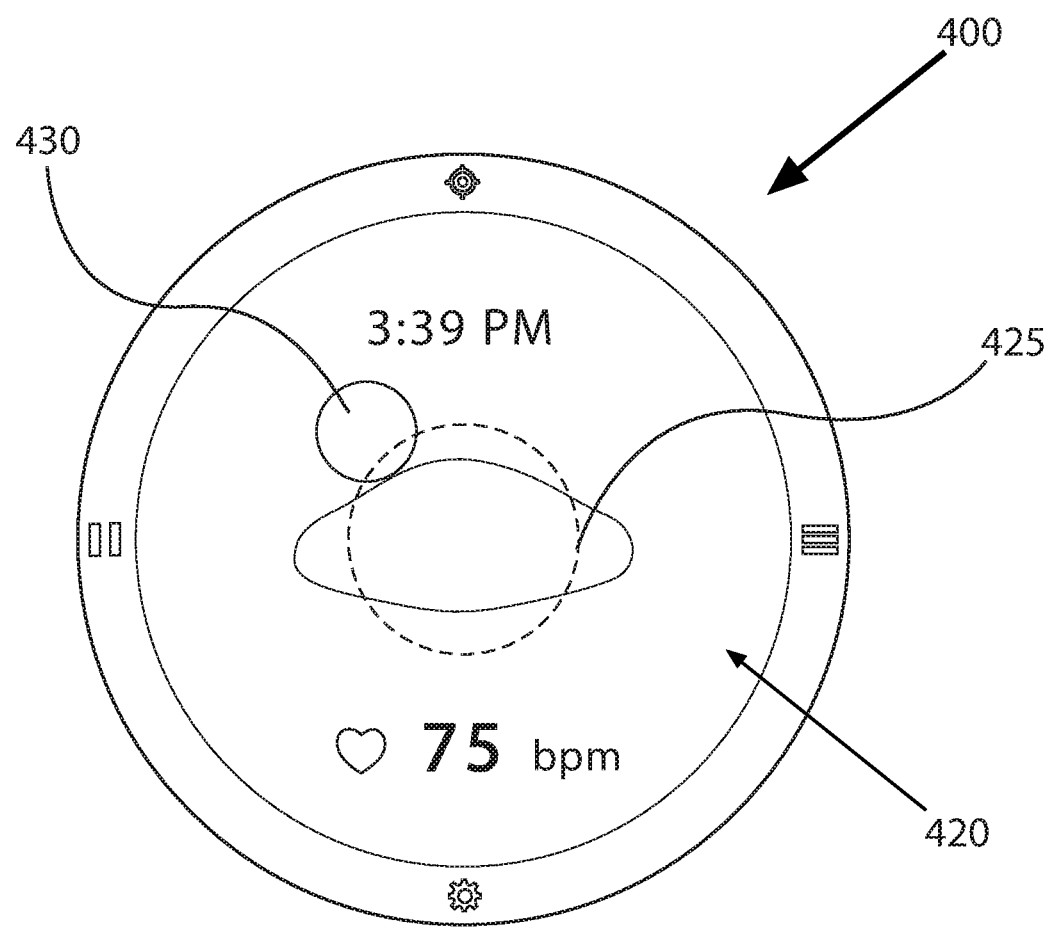
Figure 4C:
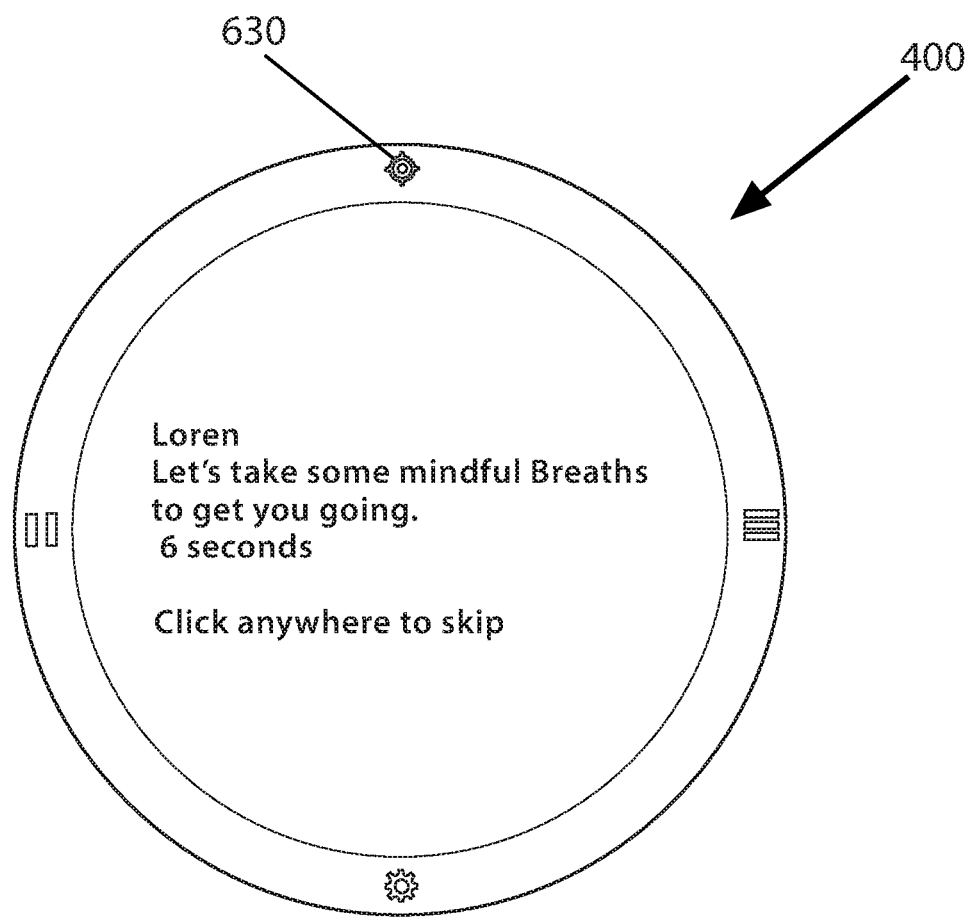

FIGS. 4A-C are illustrations of one embodiment of the posture and deep breathing improvement system interface.

Figure 5:
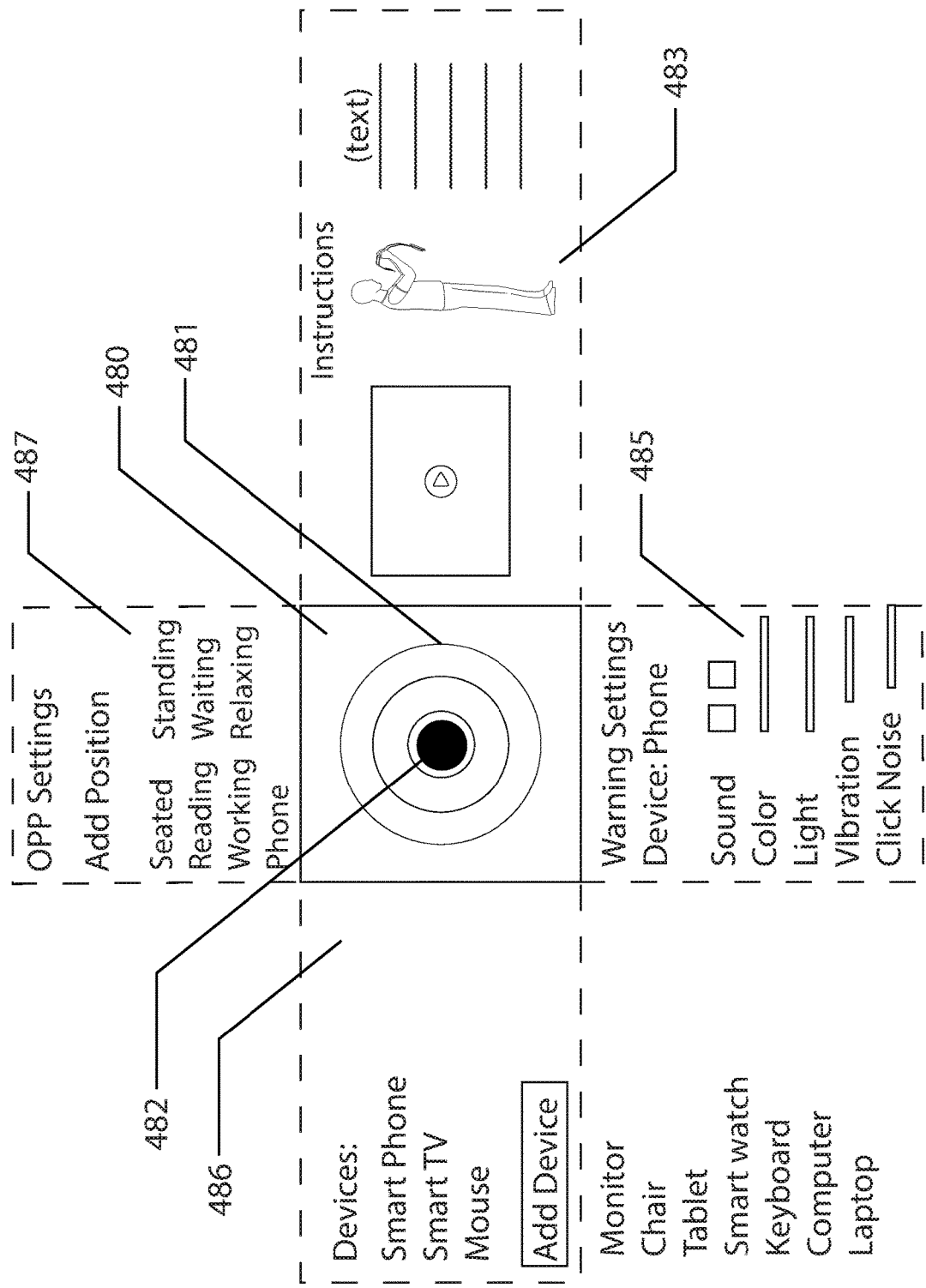

FIG. 5 is an illustration of one embodiment of deep breathing dynamic interface.

Figure 6:
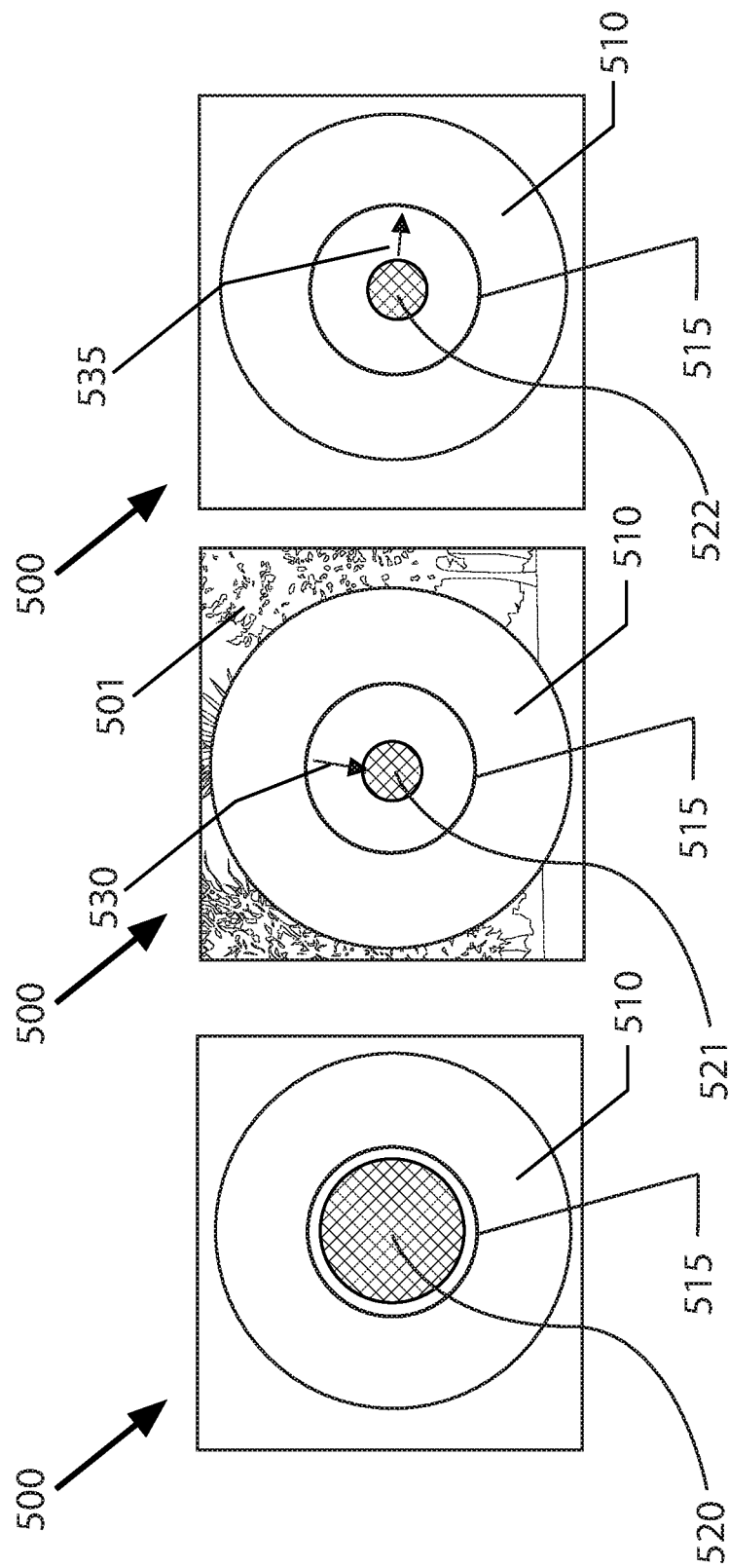

FIGS. 6A-C are illustrations of one embodiment of the posture and deep breathing improvement system interface.

Figure 7:
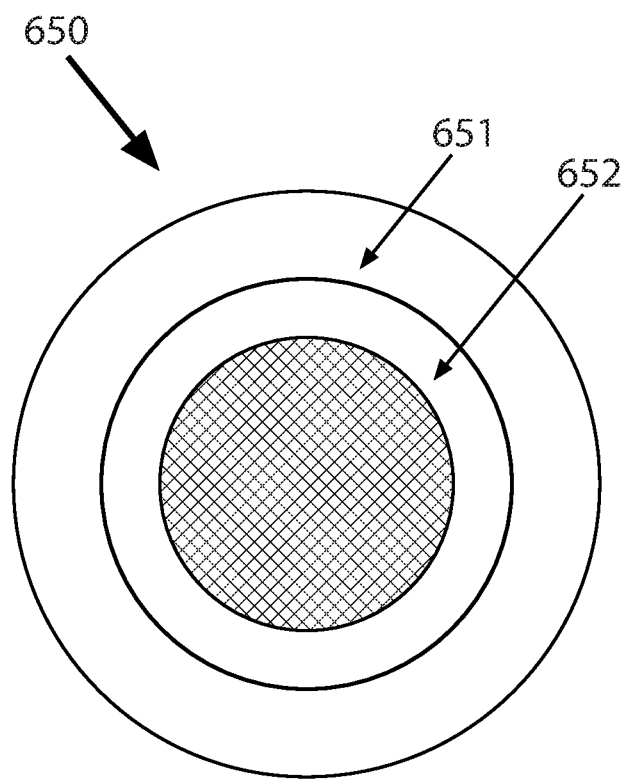

FIG. 7 is an illustration of another embodiment of the posture and deep breathing improvement system interface.

Figure 8:
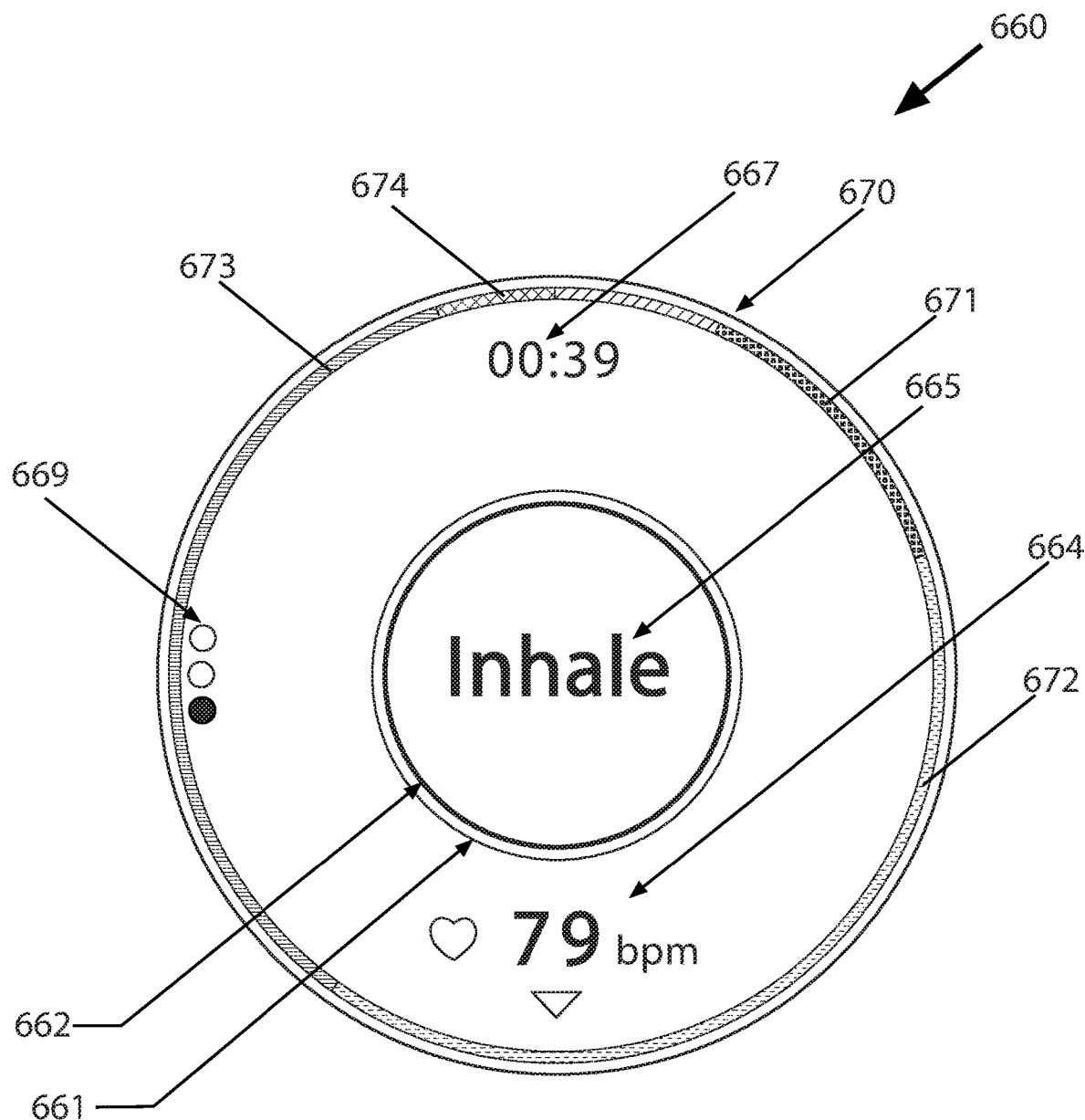

FIG. 8 is an illustration of another embodiment of the posture and deep breathing improvement system interface.

Figure 9:
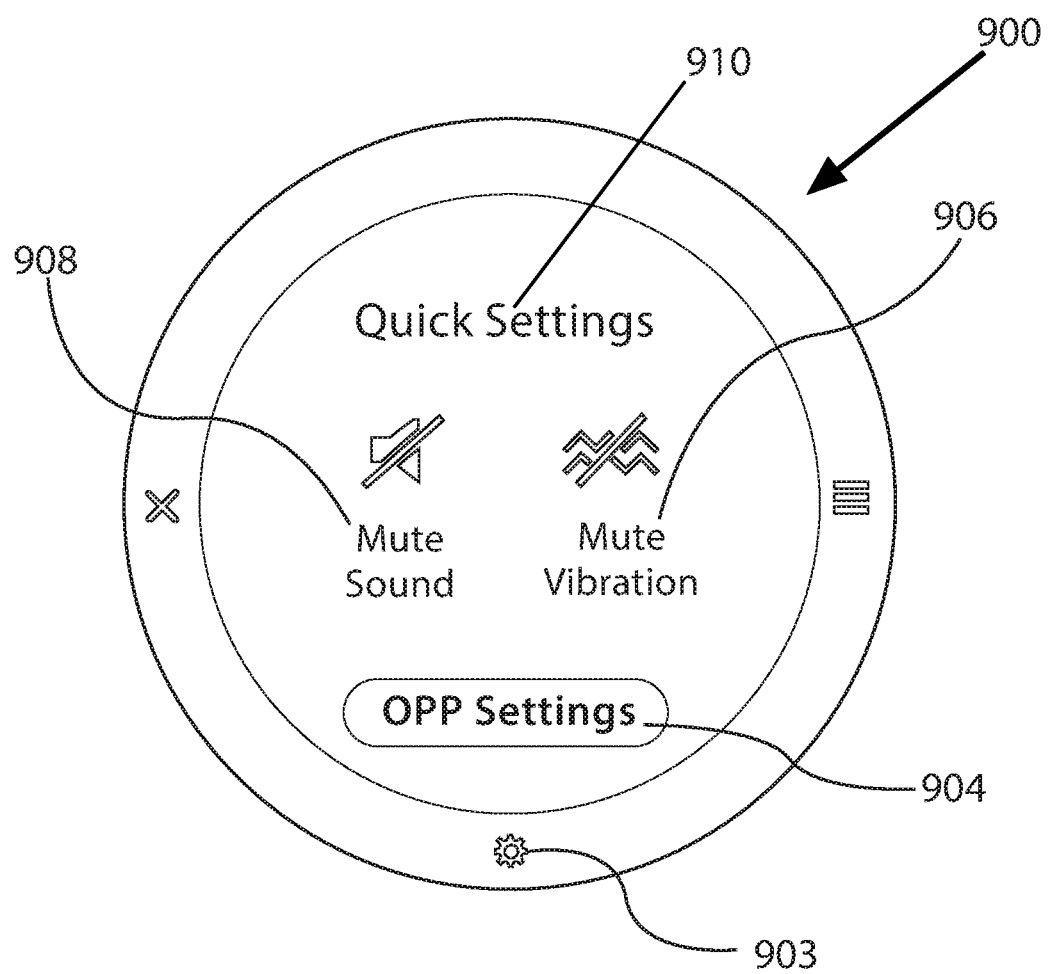

FIG. 9 is an illustration of another embodiment of the posture and deep breathing improvement system interface and shows the settings screen.

Figure 10:
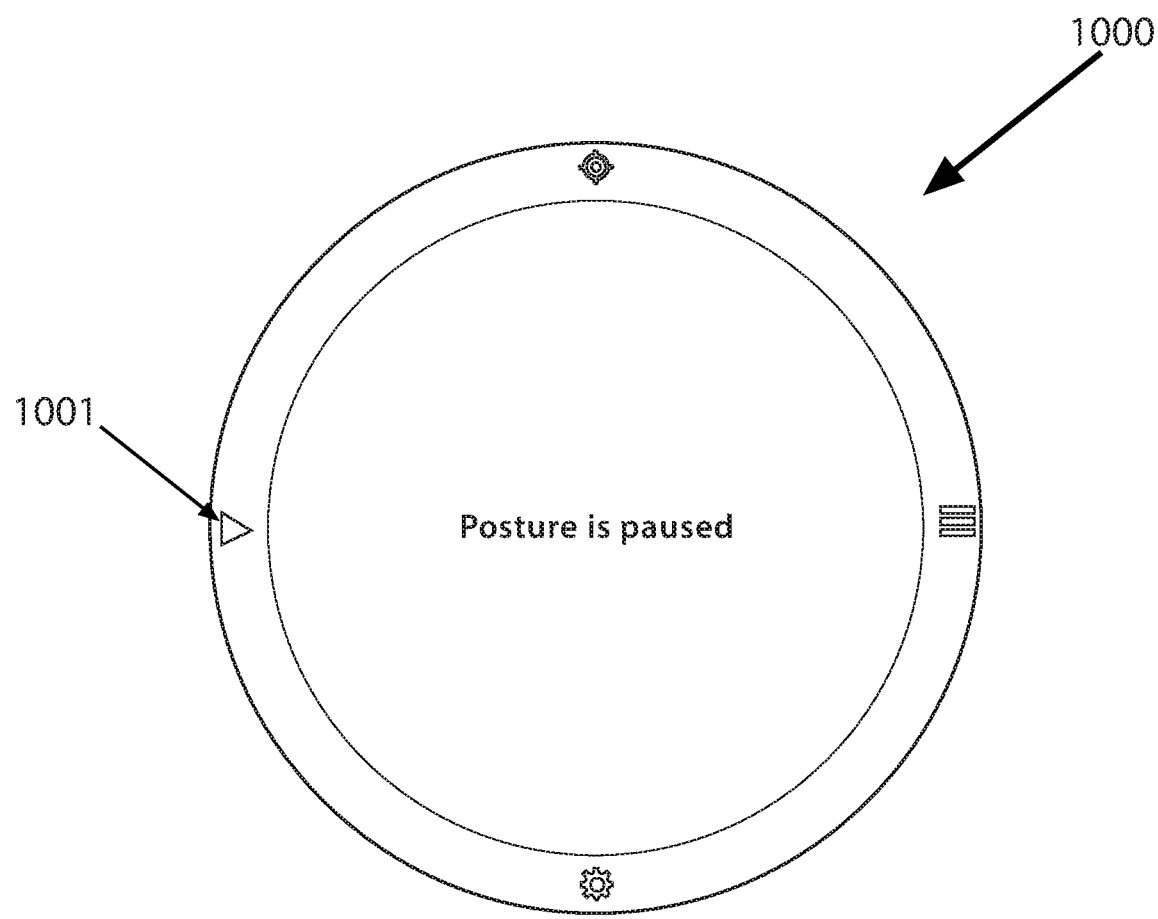

FIG. 10 is an illustration of another embodiment of the posture and deep breathing improvement system interface and shows the pause screen.

Figure 11:
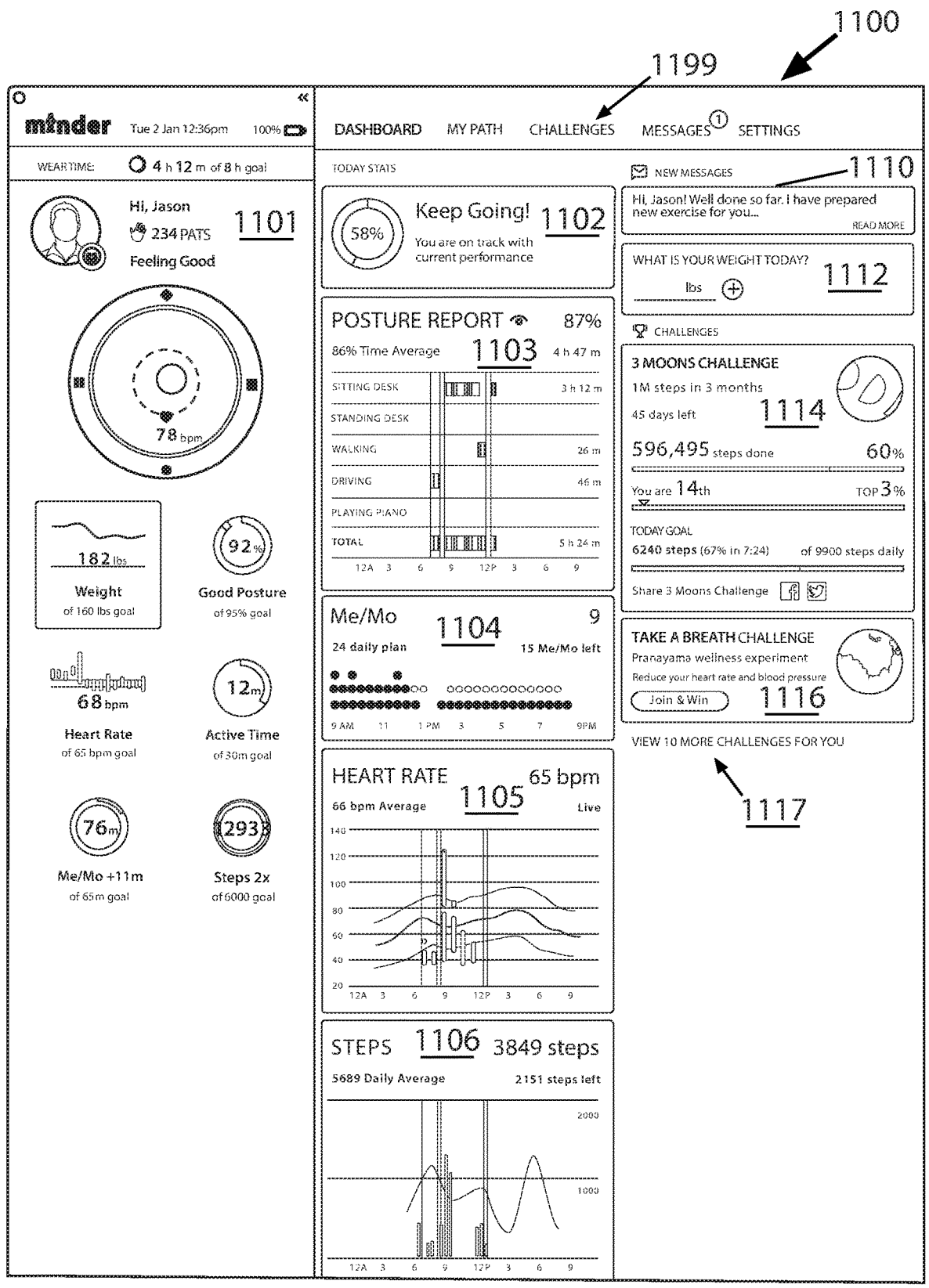

FIG. 11 is an illustration of another embodiment of the posture and deep breathing improvement system interface and shows the dashboard screen.

Figure 12:
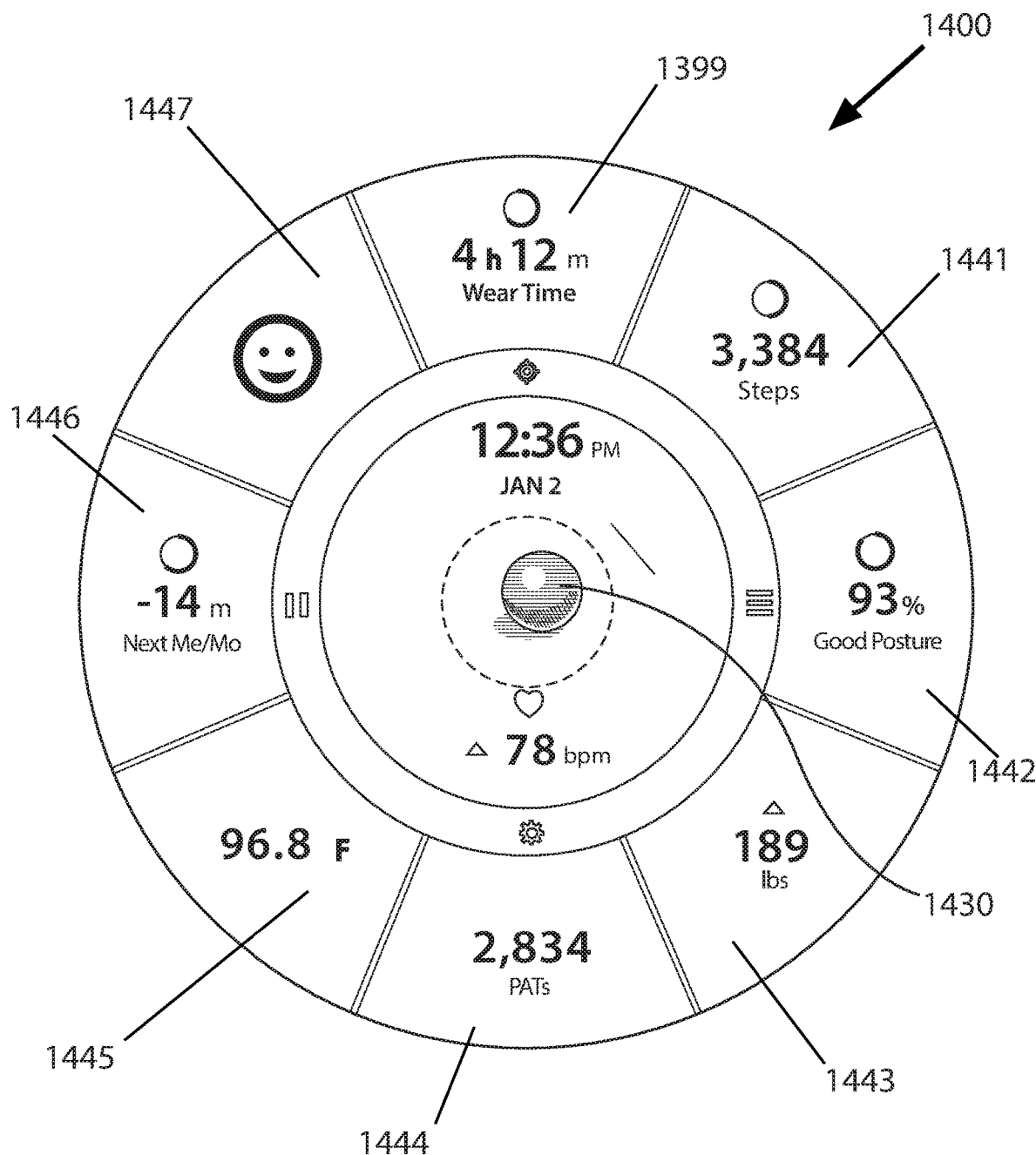

FIG. 12 is an illustration of another embodiment of the posture and deep breathing improvement system interface and shows the HUD screen.

Figure 13:
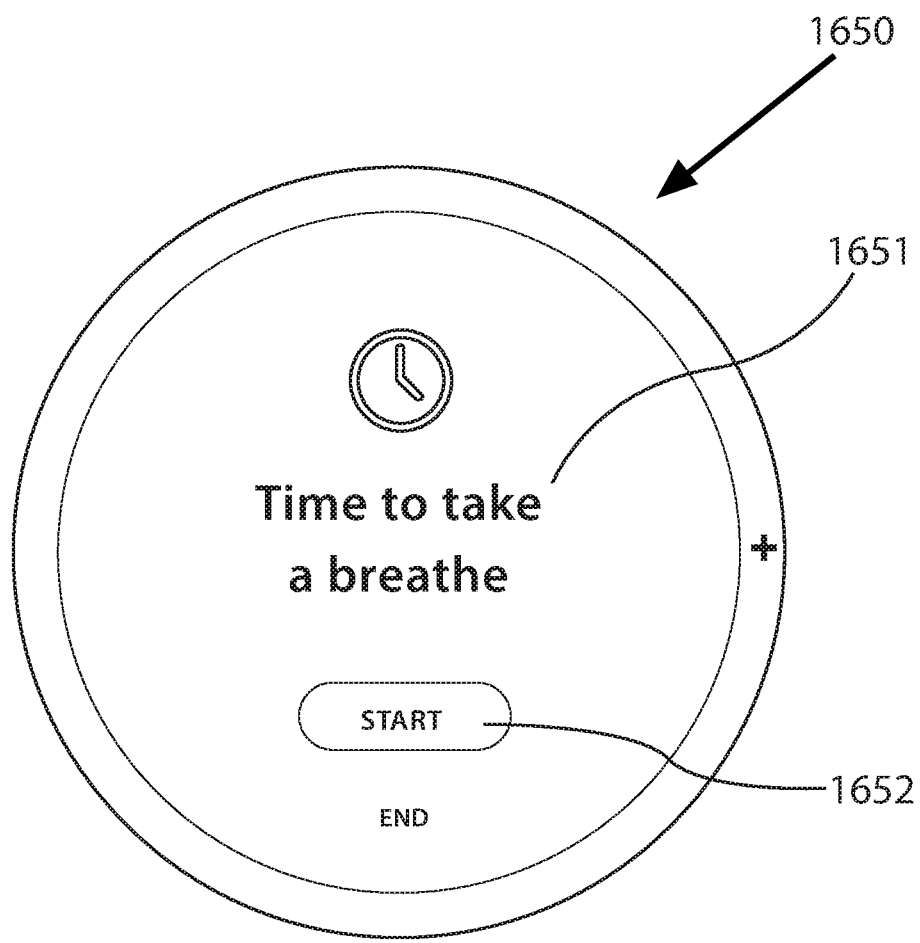

FIG. 13 is an illustration of another embodiment of the posture and deep breathing improvement system interface and shows the Me/Mo screen.

Figure 14:
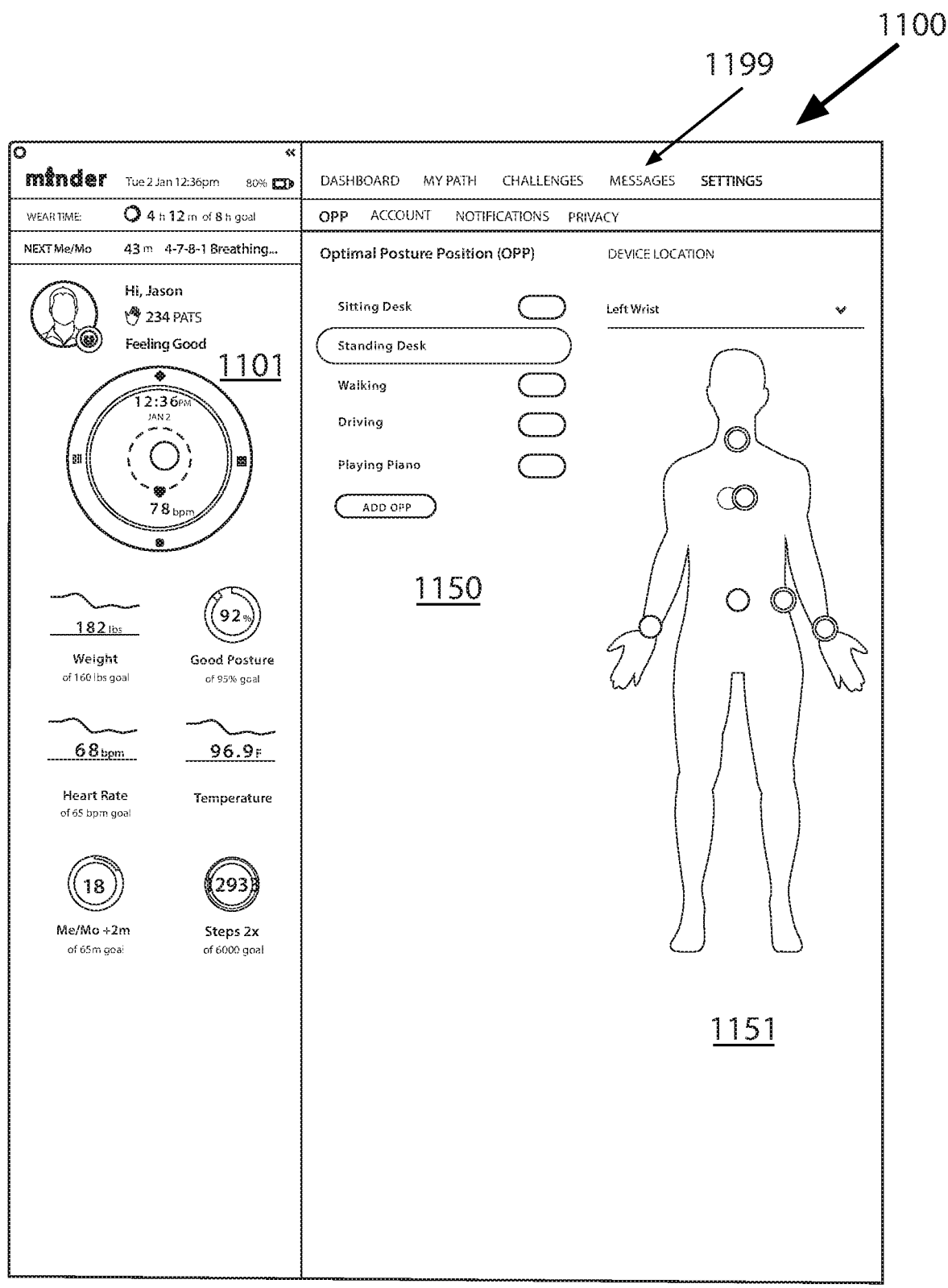

FIG. 14 is an illustration of another embodiment of the posture and deep breathing improvement system interface and shows the dashboard settings screen.

Figure 15:
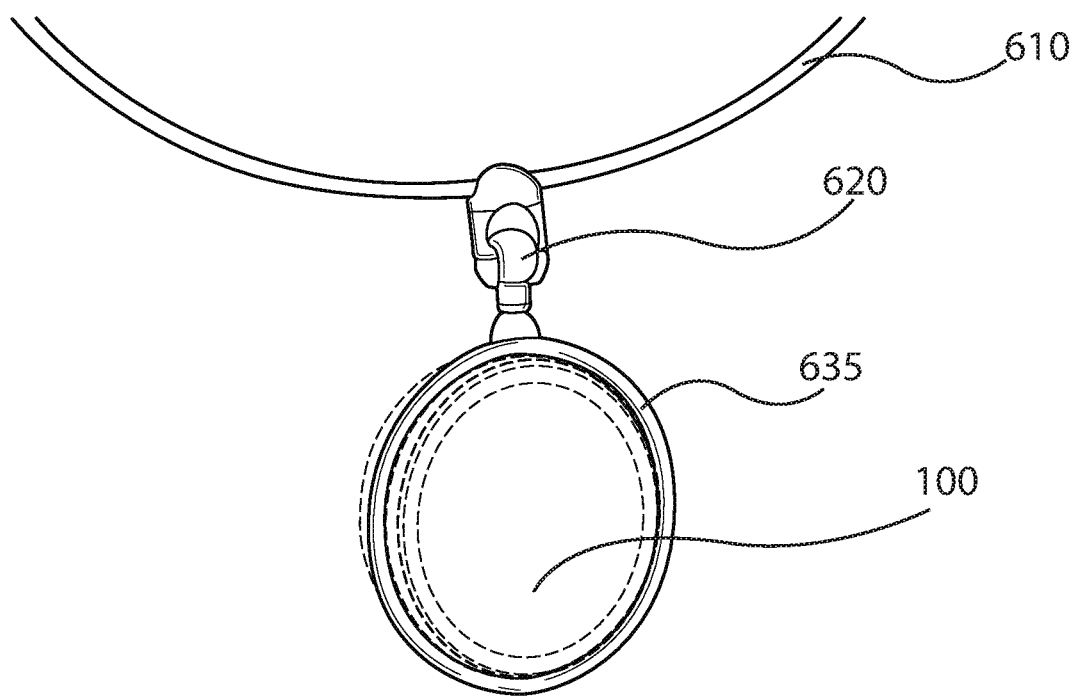

FIG. 15 is an illustration of one embodiment of a holder and harness for the sensor device.

Figure 16:
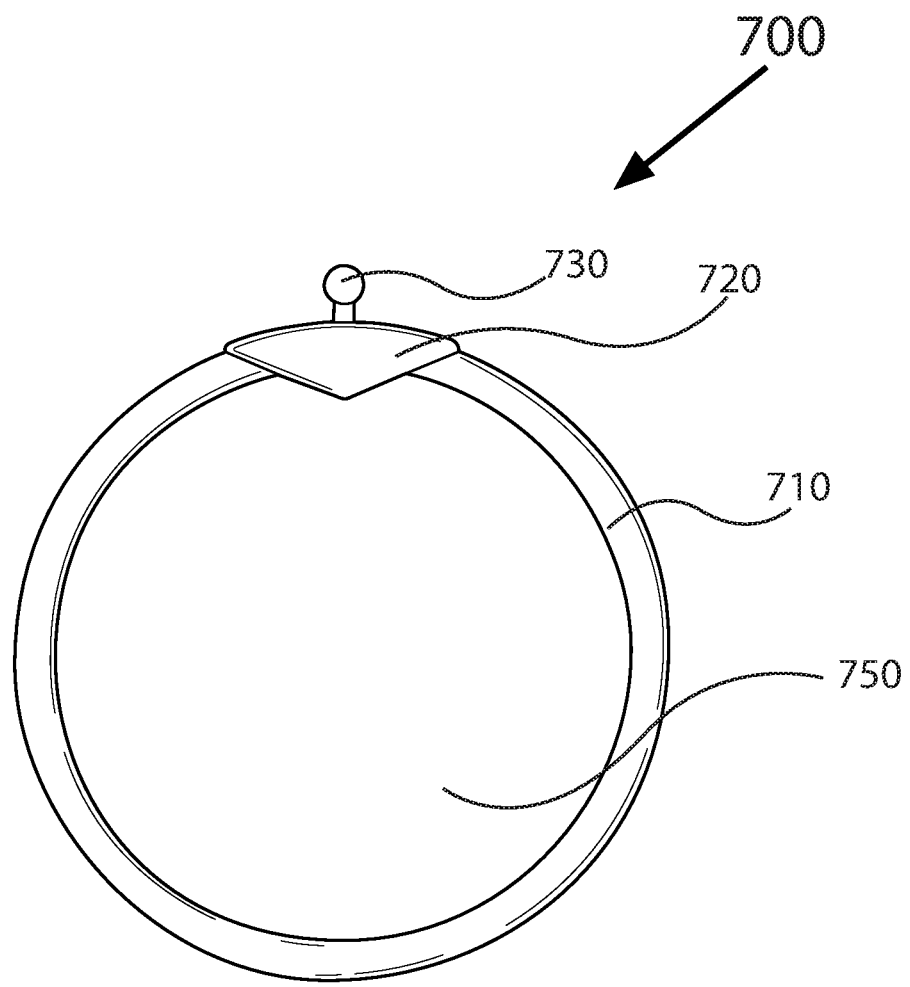

FIG. 16 is an illustration of one embodiment of a holder for the sensor device.

Figure 17:
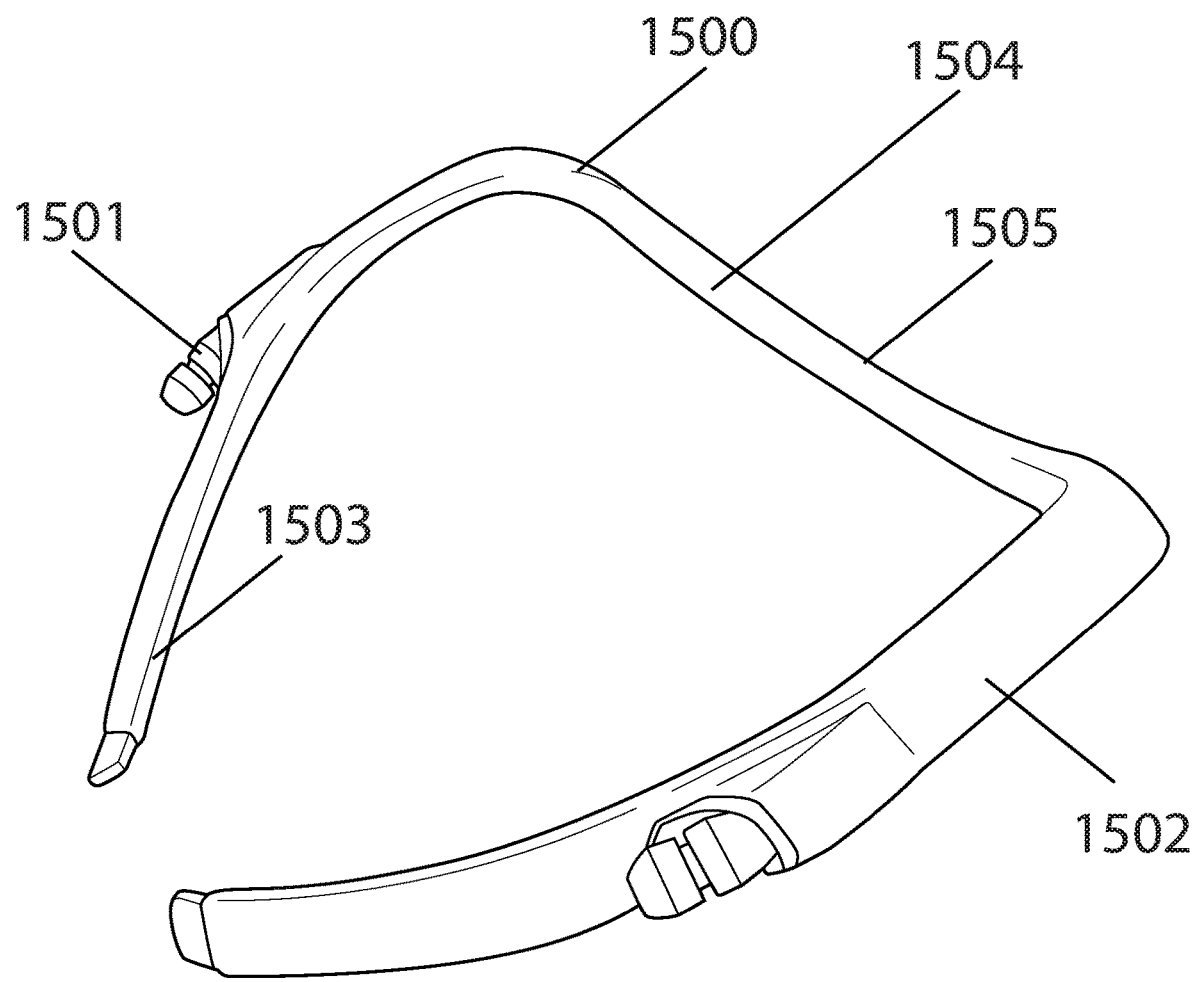

FIG. 17 is an illustration of one embodiment of a poseable harness.

Figure 18:
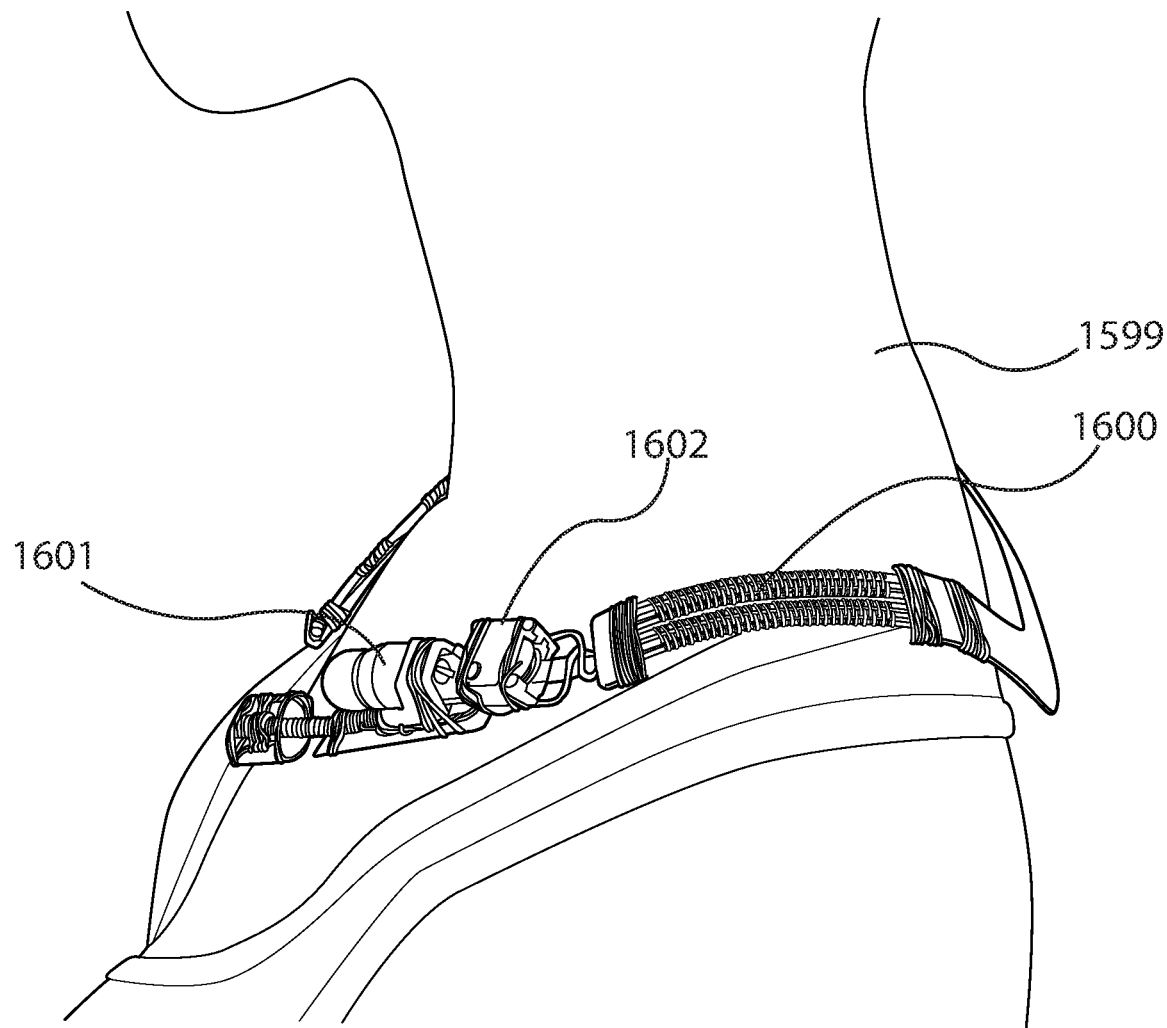

FIG. 18 is an illustration of one embodiment of a poseable harness showing retractable headphones.

Figure 19:
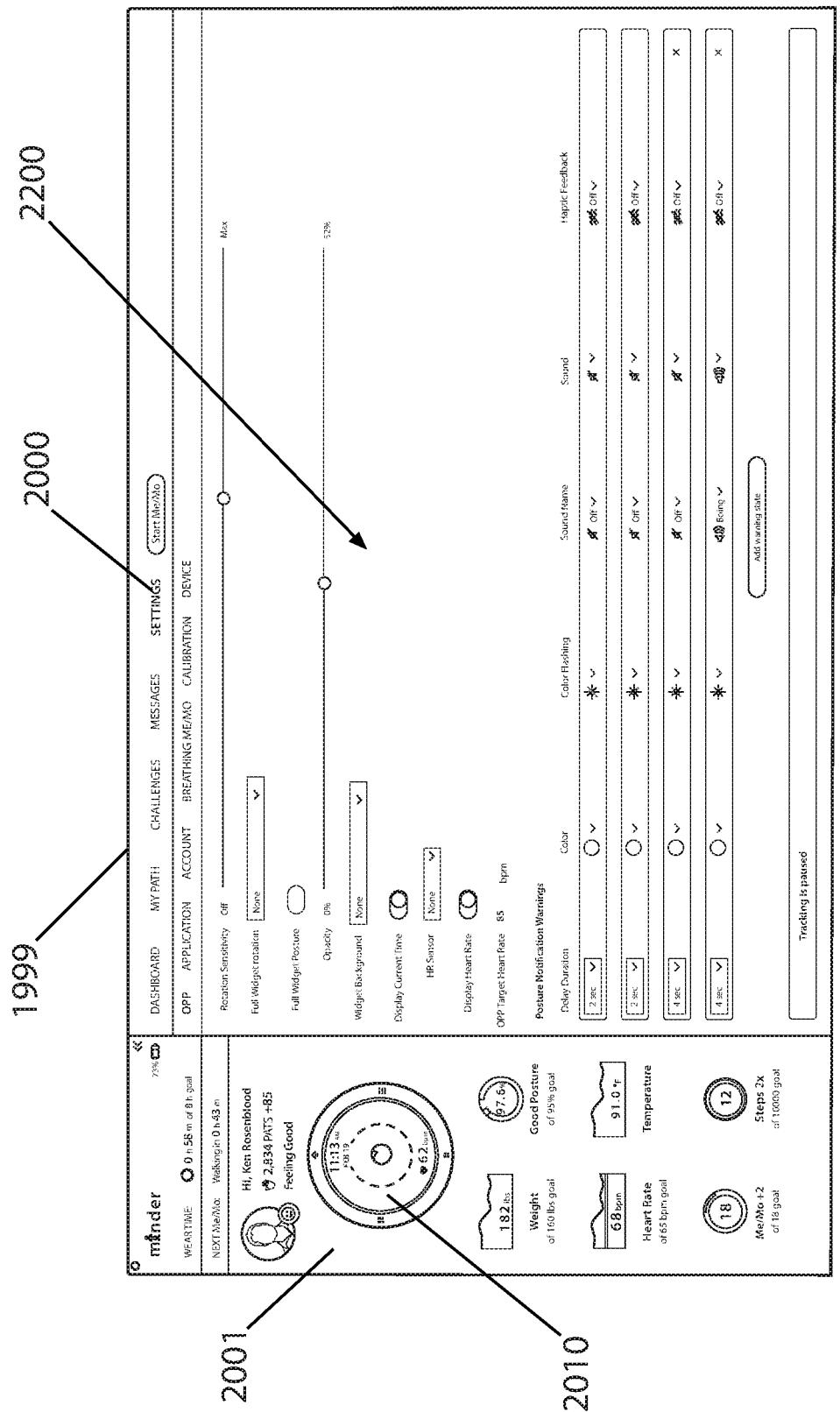

FIG. 19 is an illustration of another embodiment of the posture and deep breathing improvement system interface and shows the settings screen.

Figure 20:
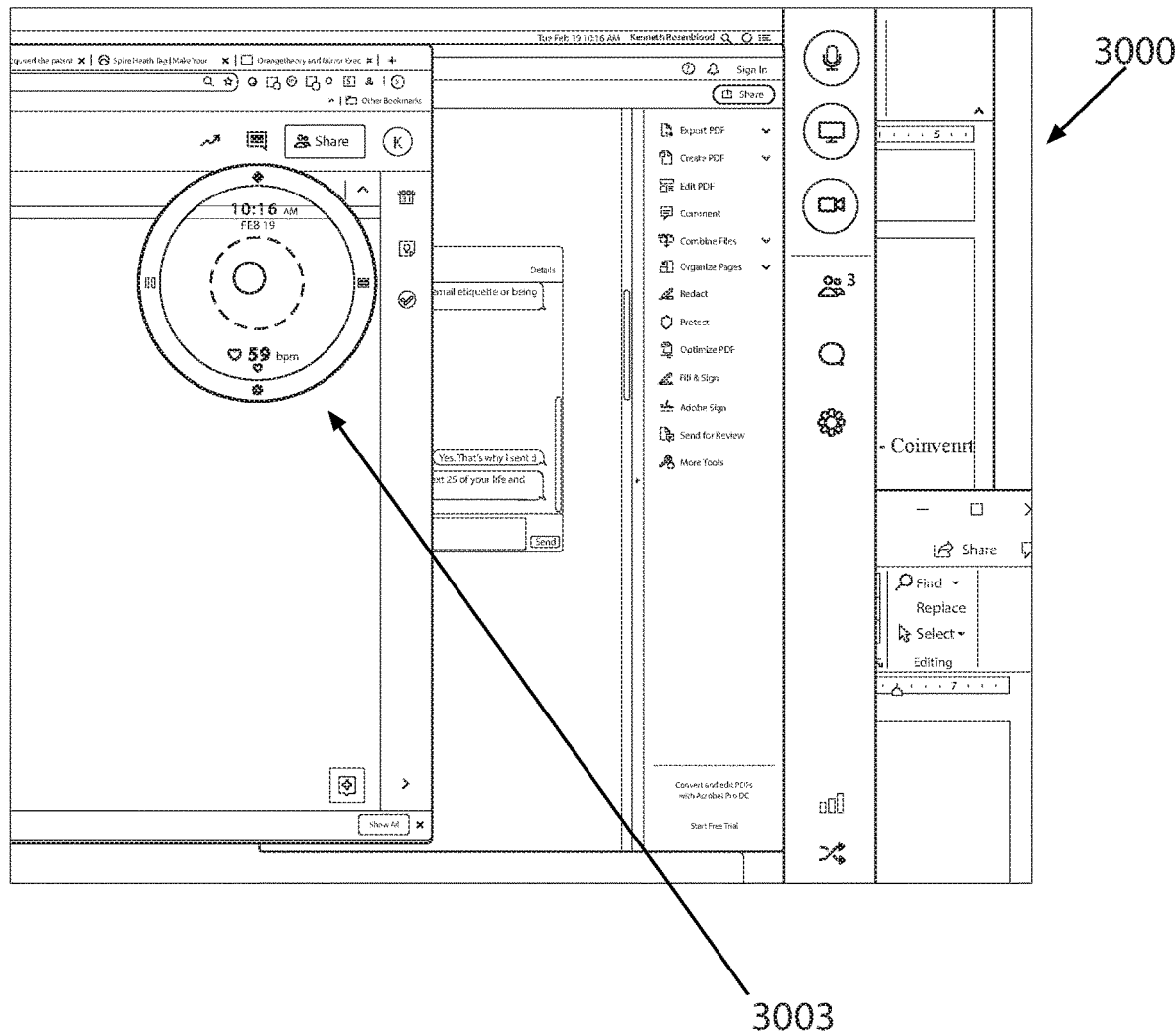

FIG. 20 is an illustration of another embodiment of the posture and deep breathing improvement system interface and shows the display may always be positioned in a screen foreground, regardless of what other programs are running on the computer.

Figure 21:
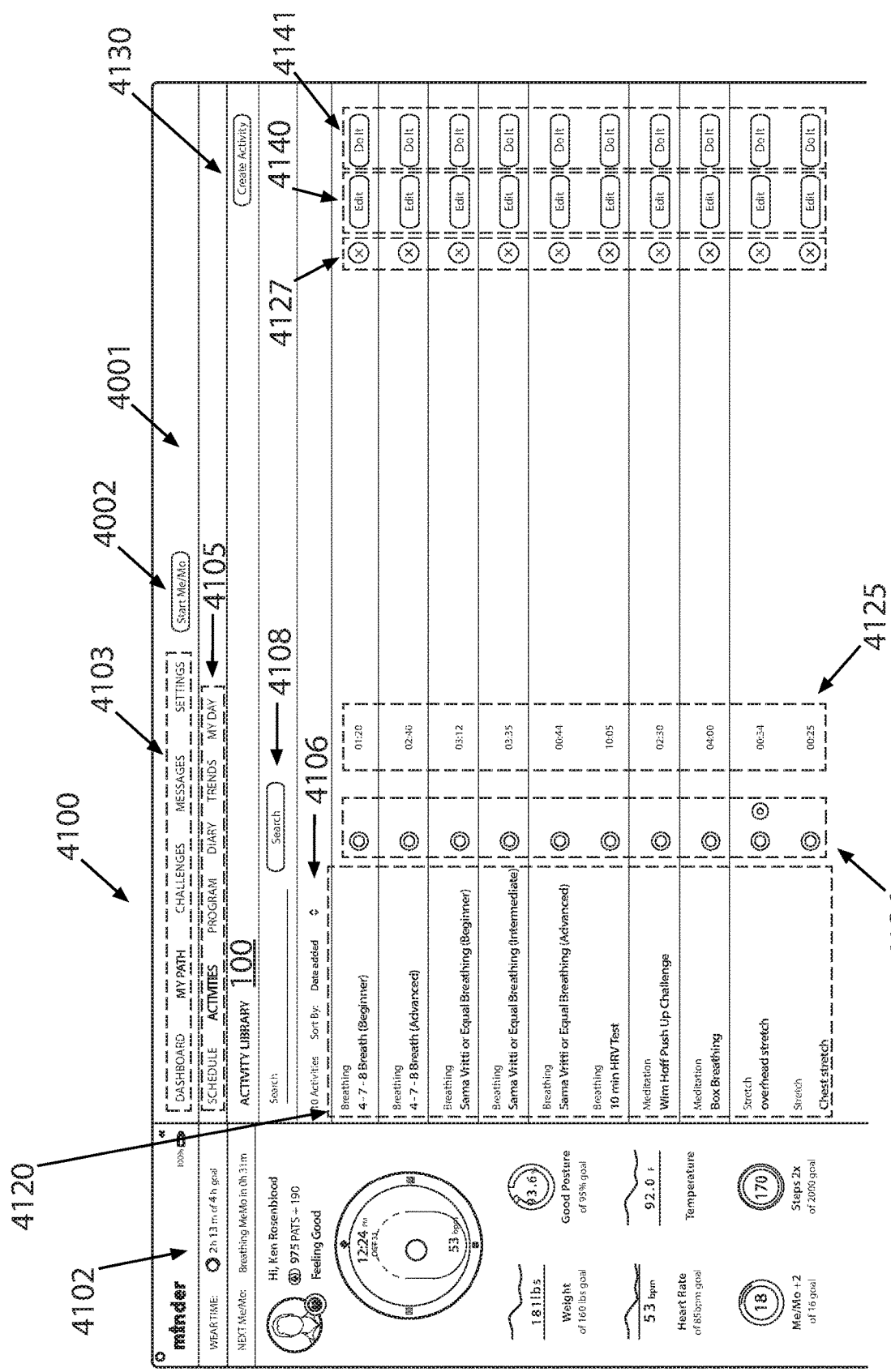

FIG. 21 is an illustration of another embodiment of the posture and deep breathing improvement system interface and shows the activity library screen.

Figure 22:
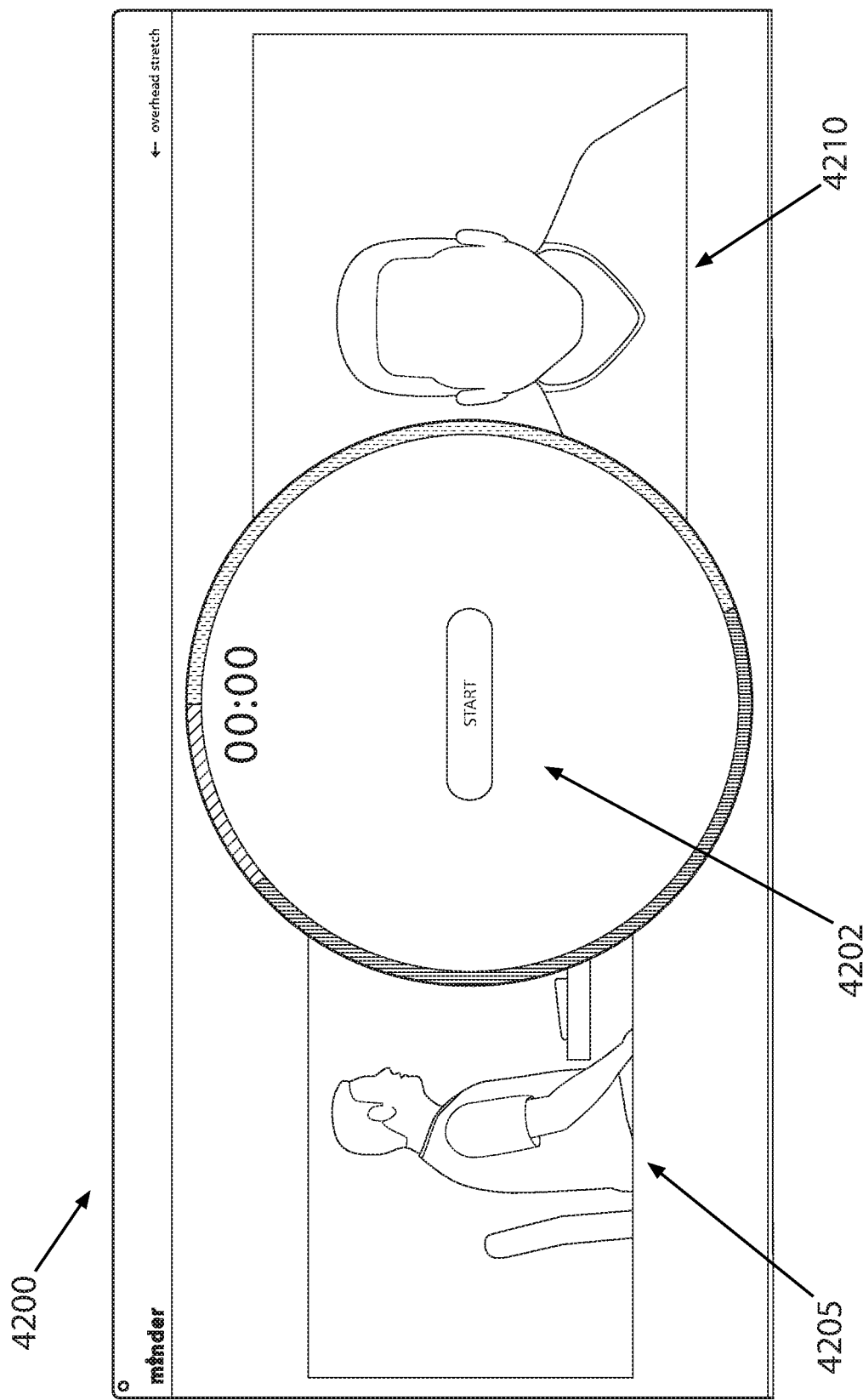

FIG. 22 is an illustration of another embodiment of the posture and deep breathing improvement system interface and shows the dual camera real time activity tracking screen.

Figure 23:
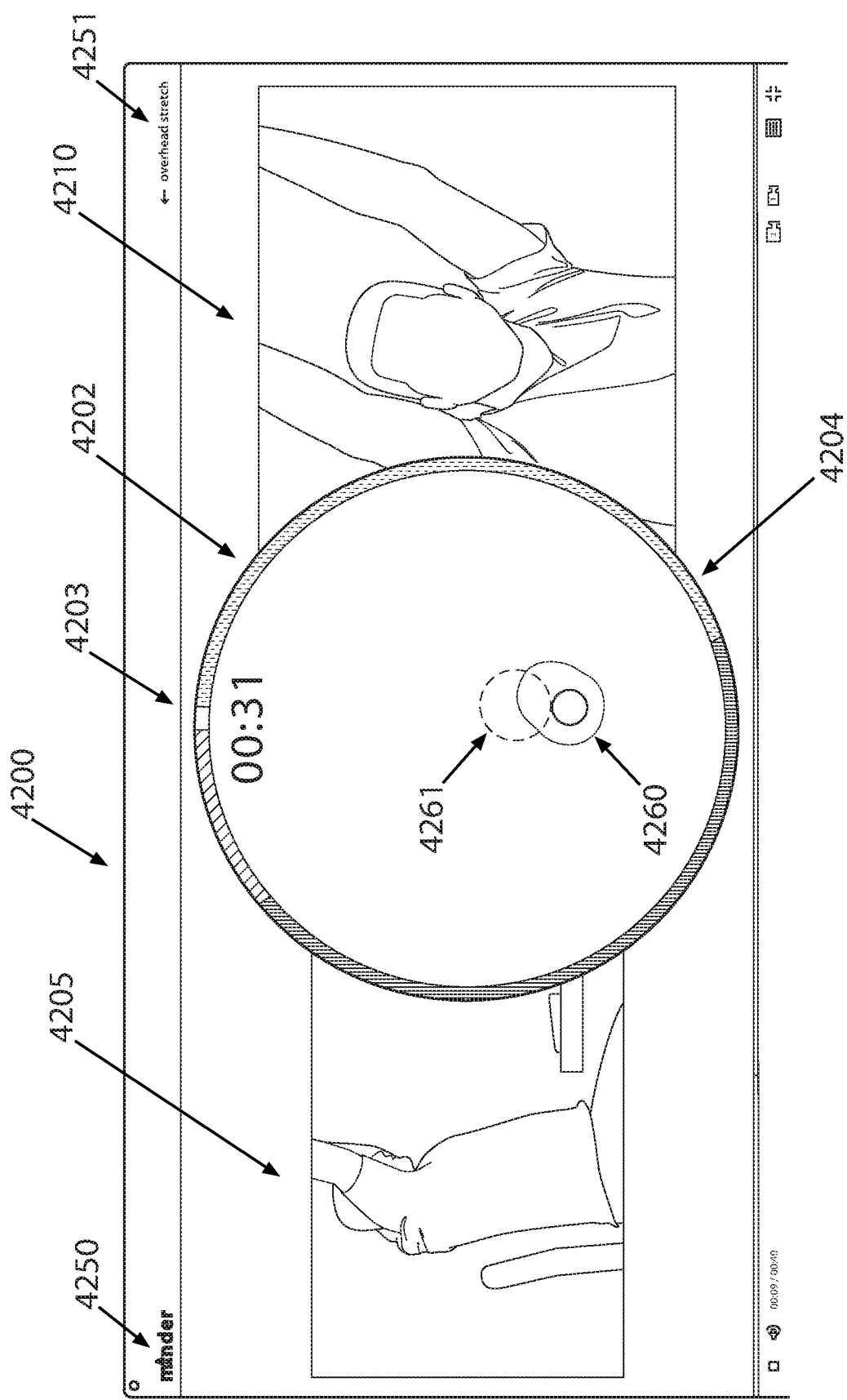

FIG. 23 is an illustration of another embodiment of the posture and deep breathing improvement system interface and shows the dual camera real time activity tracking screen with an ongoing activity being tracked by cameras and the device.

Figure 24:
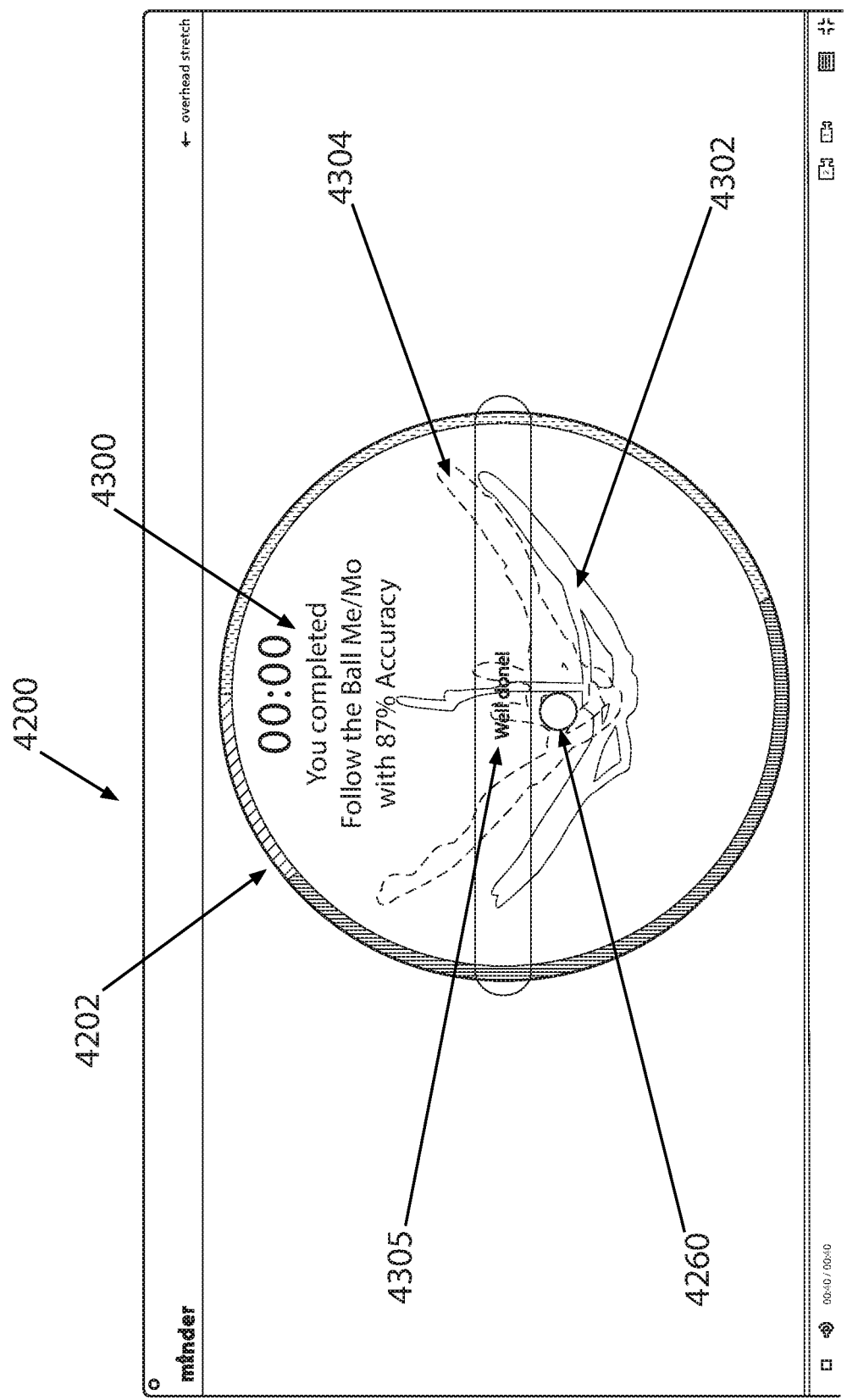

FIG. 24 is an illustration of another embodiment of the posture and deep breathing improvement system interface and shows the result screen showing qualitative and quantitative results.

Figure 25:
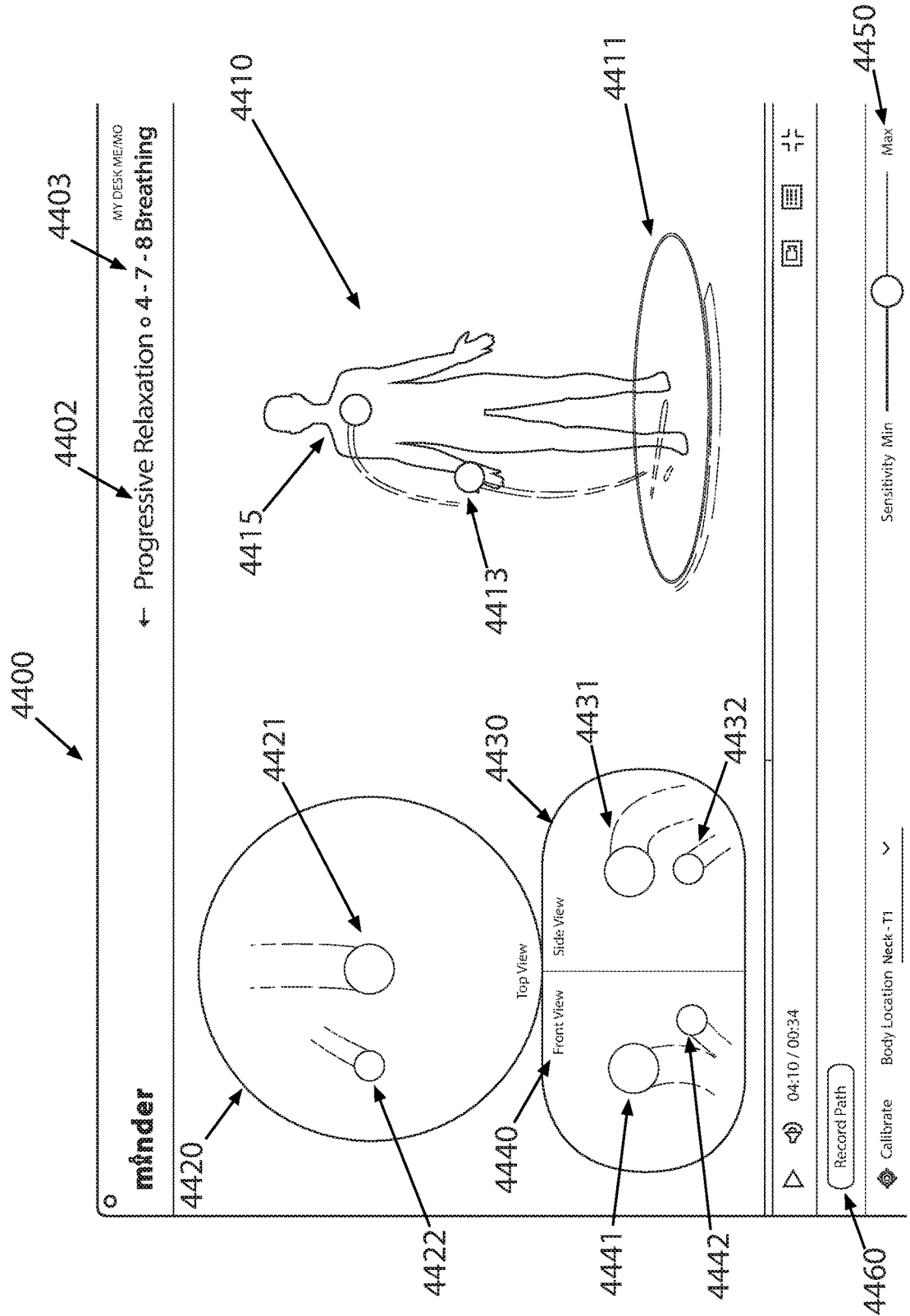

FIG. 25 is an illustration of another embodiment of the posture and deep breathing improvement system interface and shows the real time activity tracking screen with the user using and wearing two devices.

Figure 26:
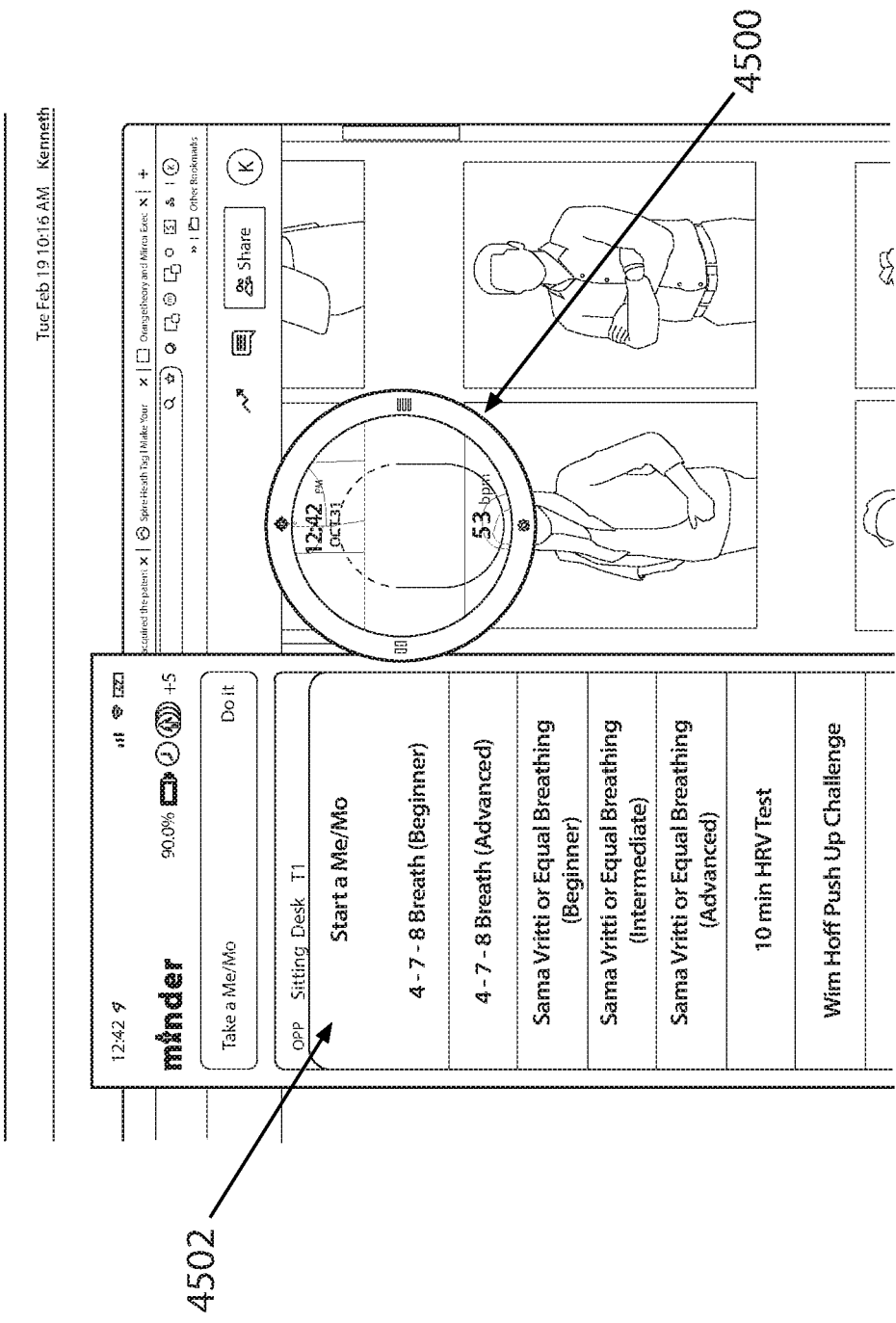

FIG. 26 is an illustration of another embodiment of the posture and deep breathing improvement system interface and shows the Start A Me/Mo pop-up, which displays a list of Me/Mos that have been created and may be selected.

Figure 27:
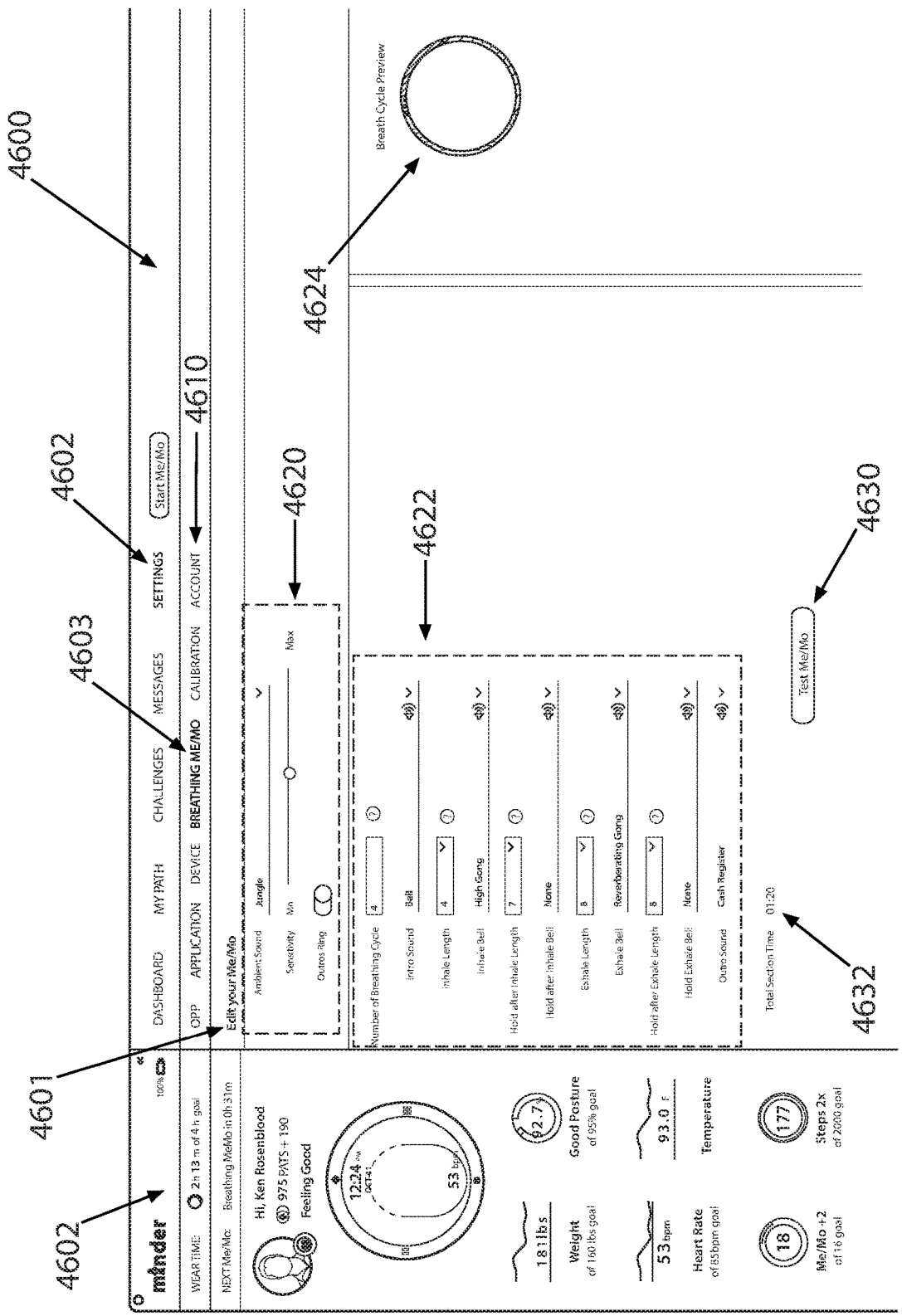

FIG. 27 is an illustration of another embodiment of the posture and deep breathing improvement system interface and shows the Edit Your Me/Mo Screen.

Figure 28:
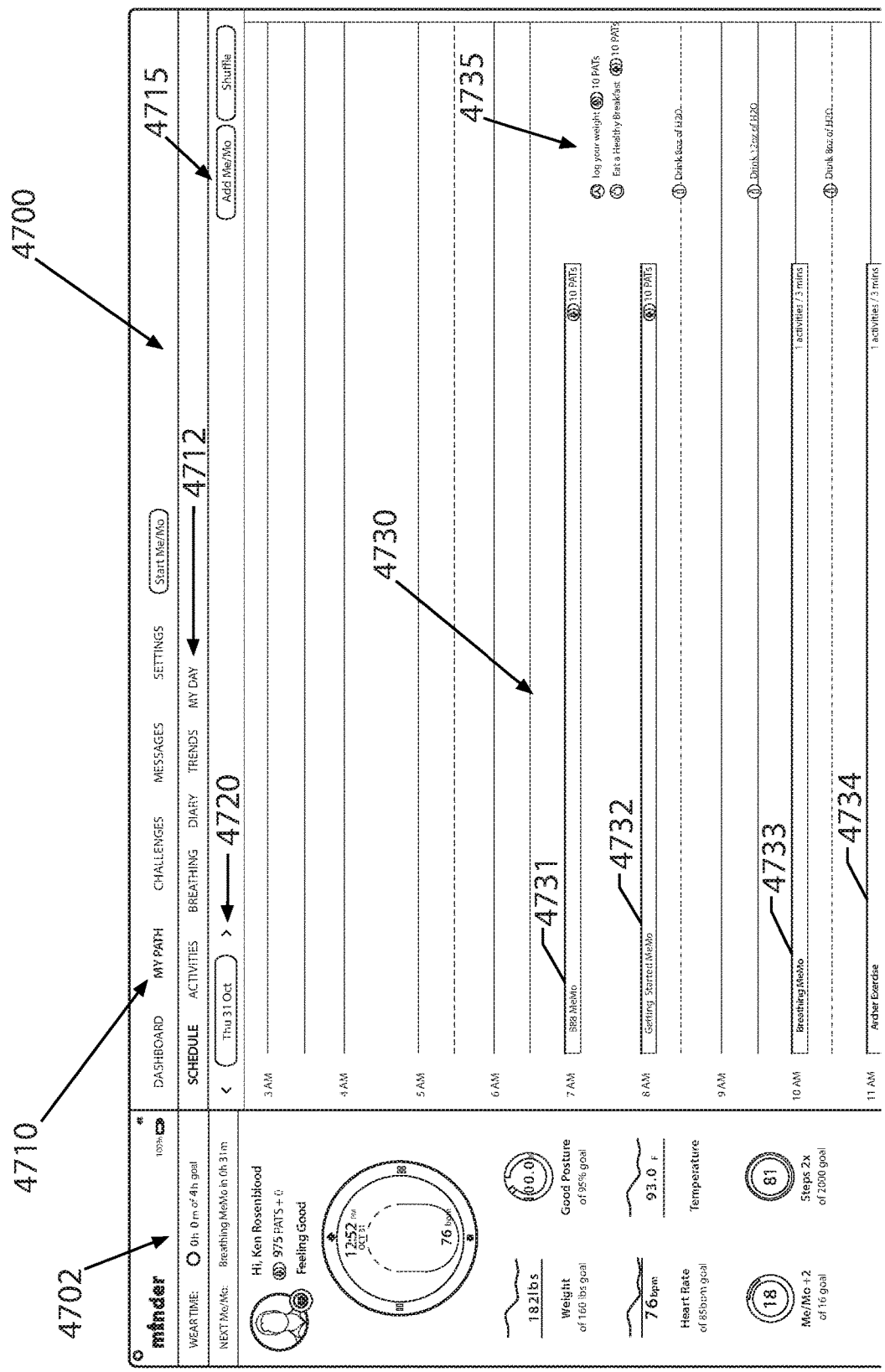

FIG. 28 is an illustration of another embodiment of the posture and deep breathing improvement system interface and shows the interactive schedule screen.

Figure 29:
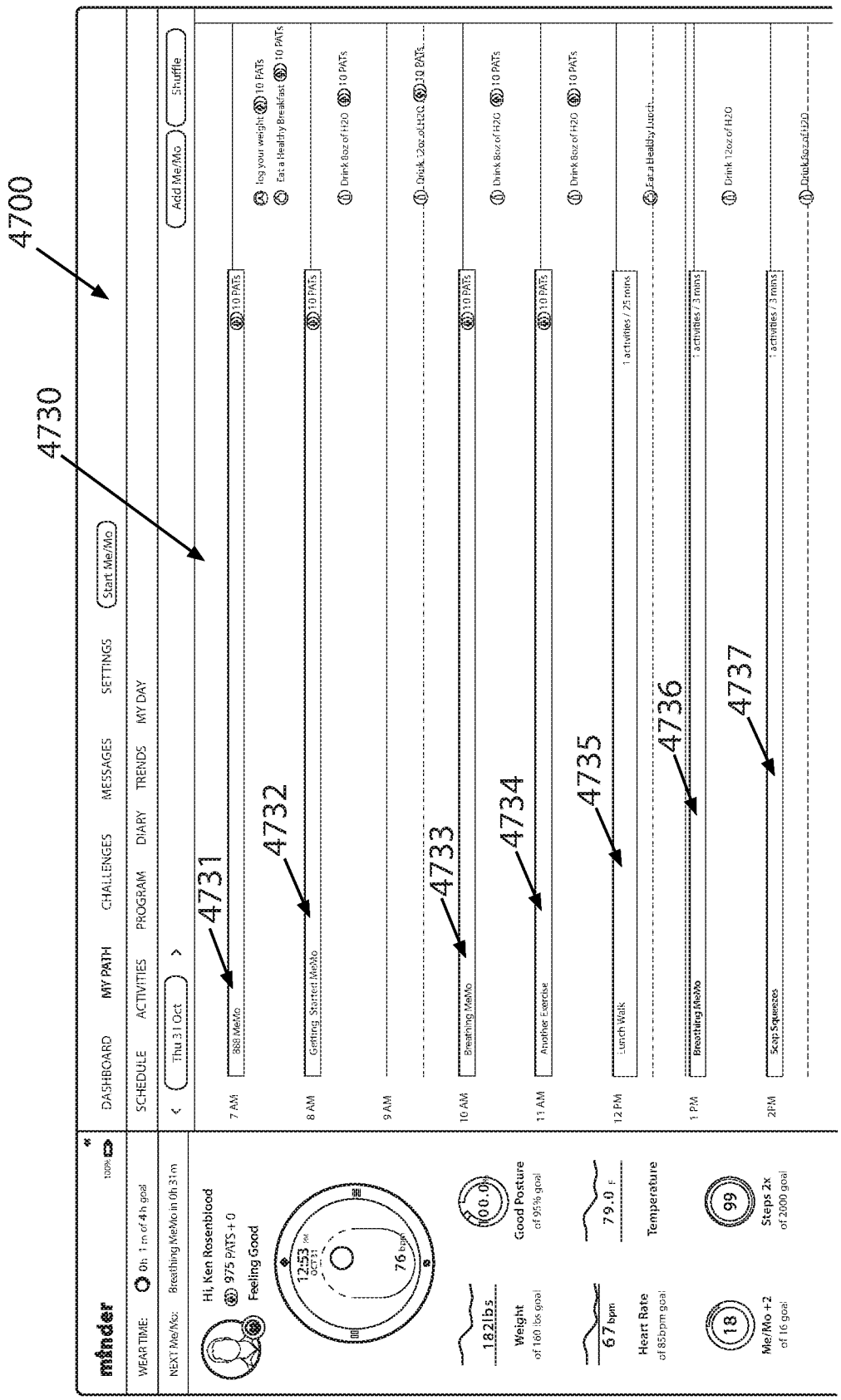

FIG. 29 is an illustration of another embodiment of the posture and deep breathing improvement system interface and shows the interactive schedule screen.

Figure 30:
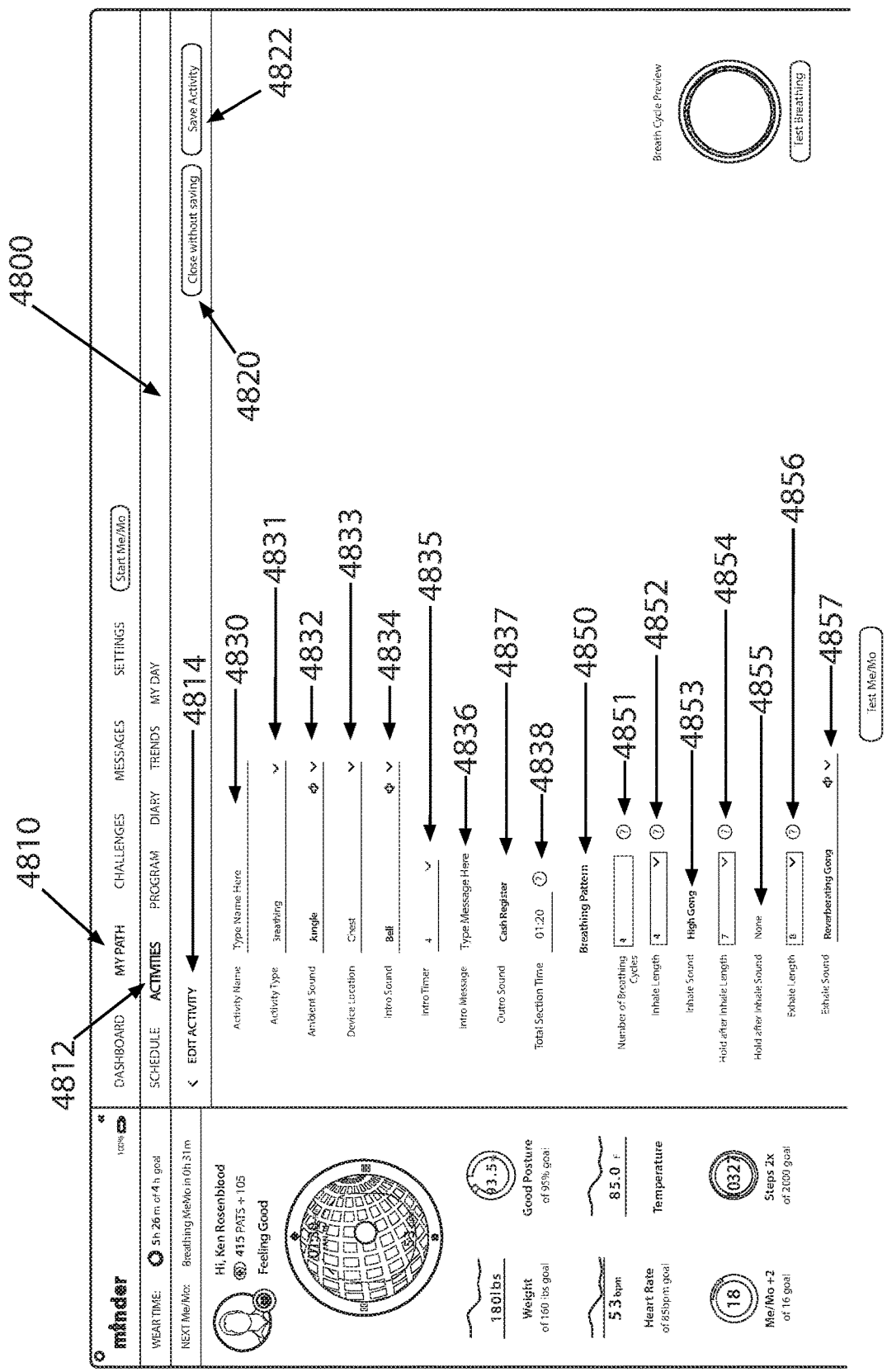

FIG. 30 is an illustration of another embodiment of the posture and deep breathing improvement system interface and shows the create an activity screen.

FIG. 31 is an illustration of another embodiment of the posture and deep breathing improvement system interface and shows the create an activity screen adding breathing to the activity.

Figure 32:
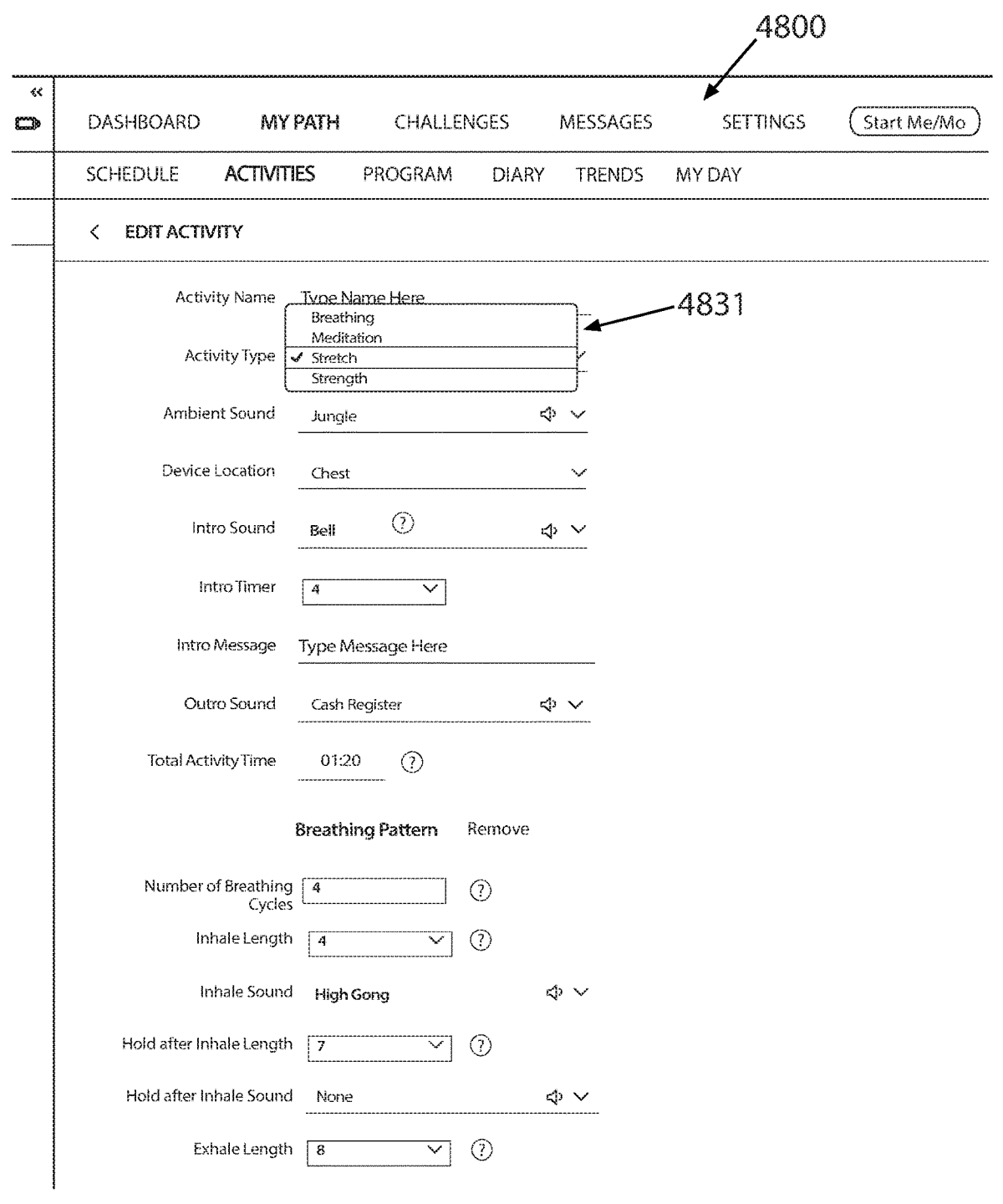

FIG. 32 is an illustration of another embodiment of the posture and deep breathing improvement system interface and shows the create an activity screen with a list of activities from which to select.

Figure 33:

FIG. 33 is an illustration of another embodiment of the posture and deep breathing improvement system interface and shows the create activity screen and selecting the follow the ball path option.

Figure 34:
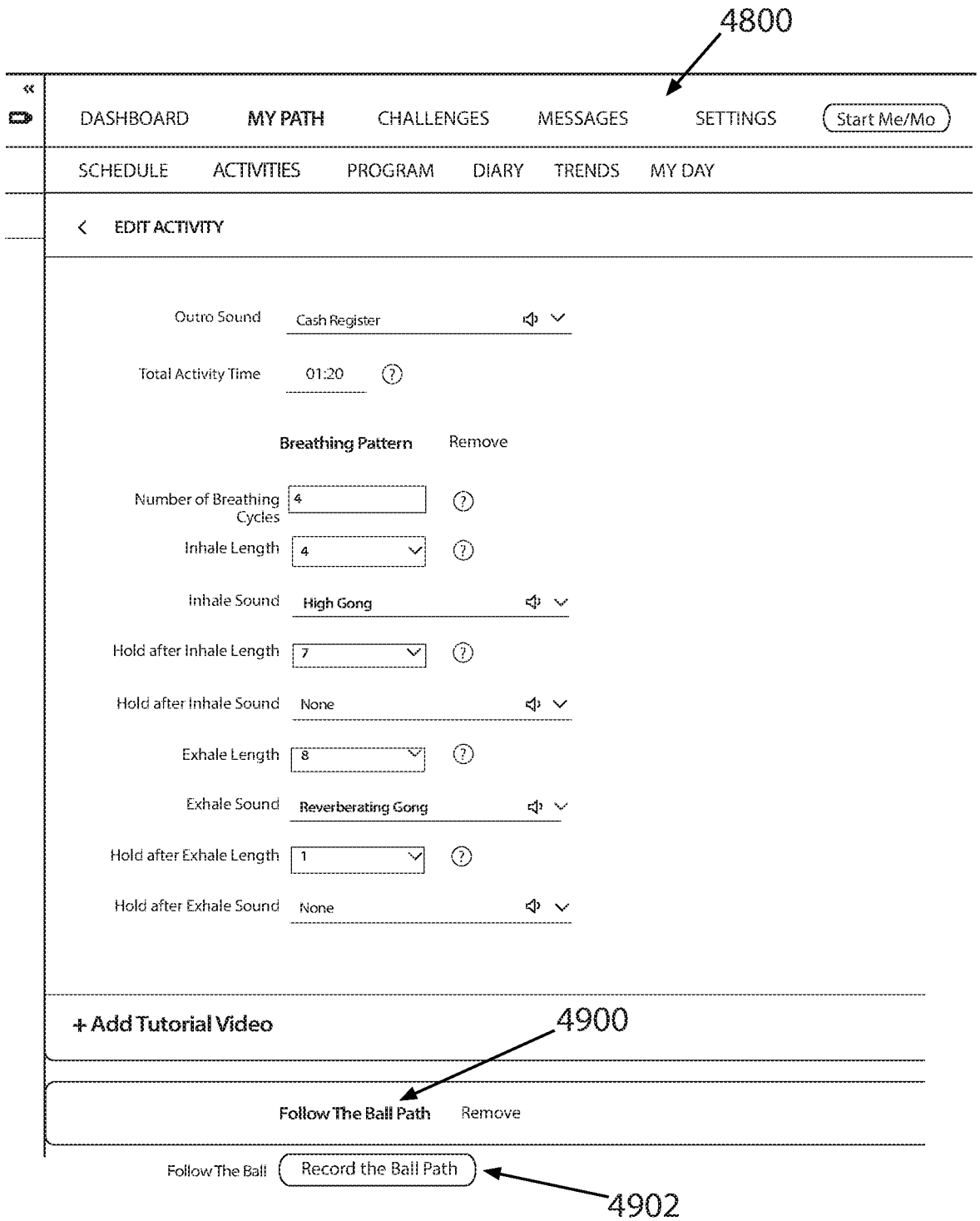

FIG. 34 is an illustration of another embodiment of the posture and deep breathing improvement system interface and shows the create activity screen and selecting the follow the ball path option selected.

Figure 35:
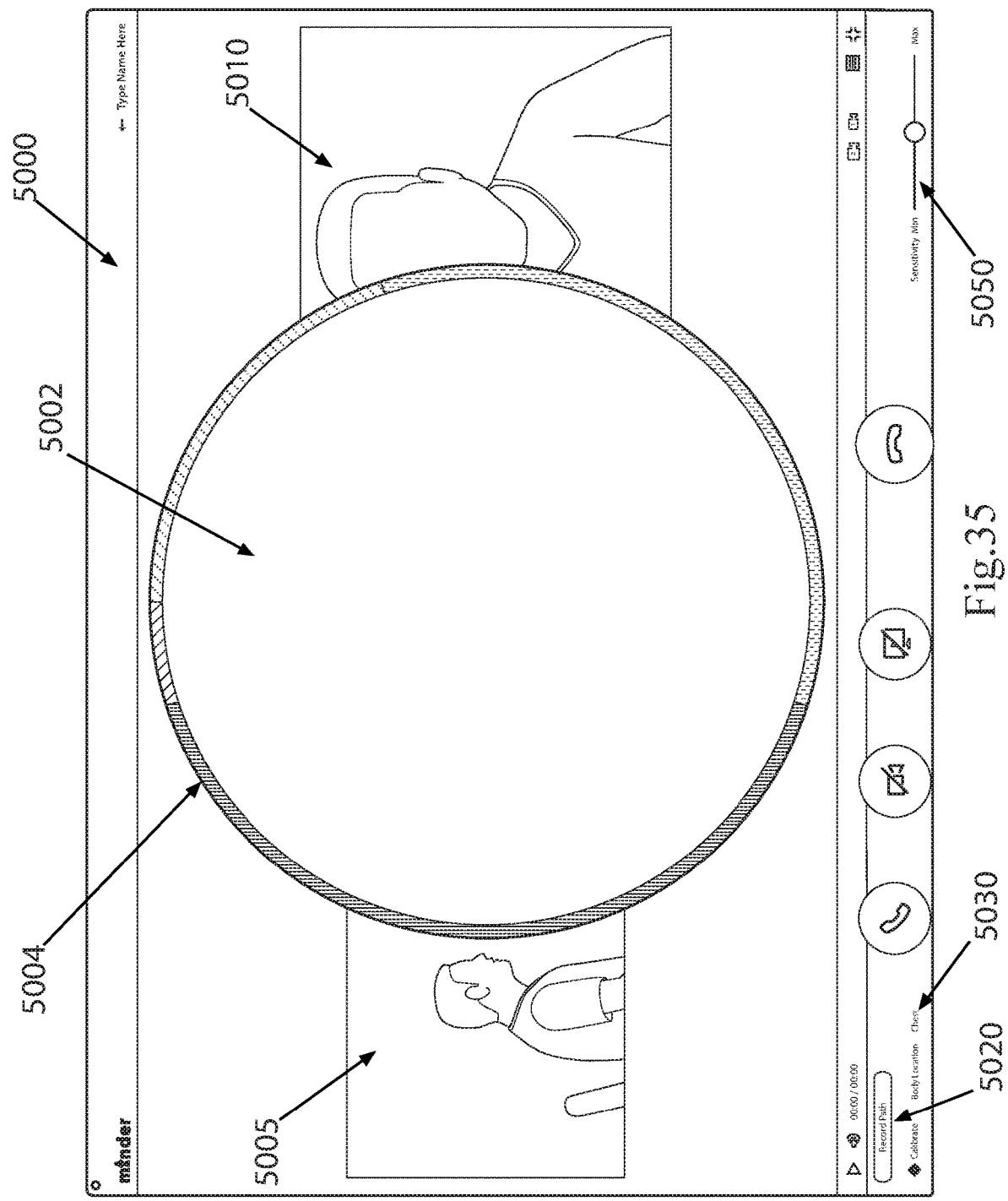

FIG. 35 is an illustration of another embodiment of the posture and deep breathing improvement system interface and shows the record the ball path start screen.

Figure 36:
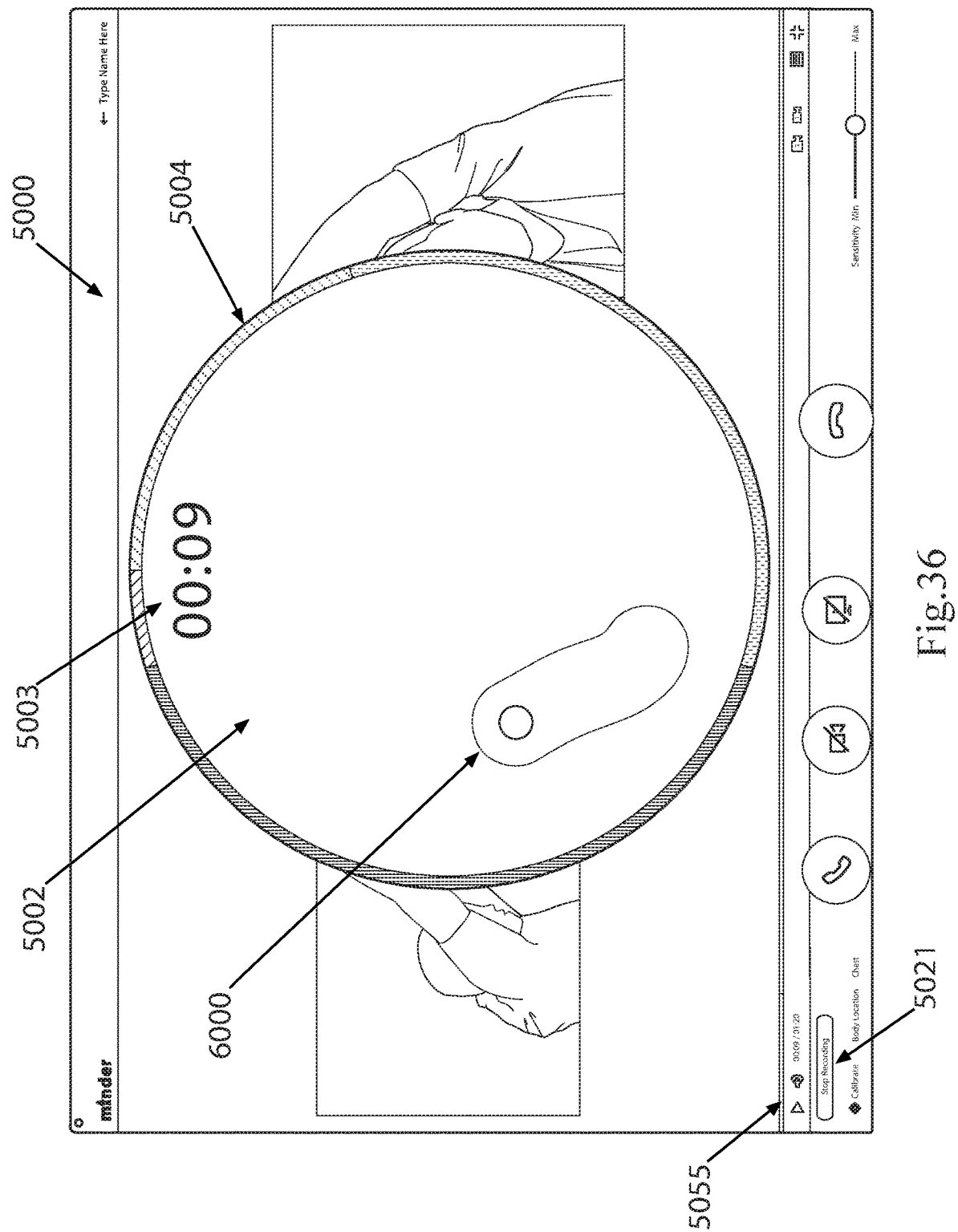

FIG. 36 is an illustration of another embodiment of the posture and deep breathing improvement system interface and shows the record the ball path being recorded while the user performs an exercise.

Figure 37:
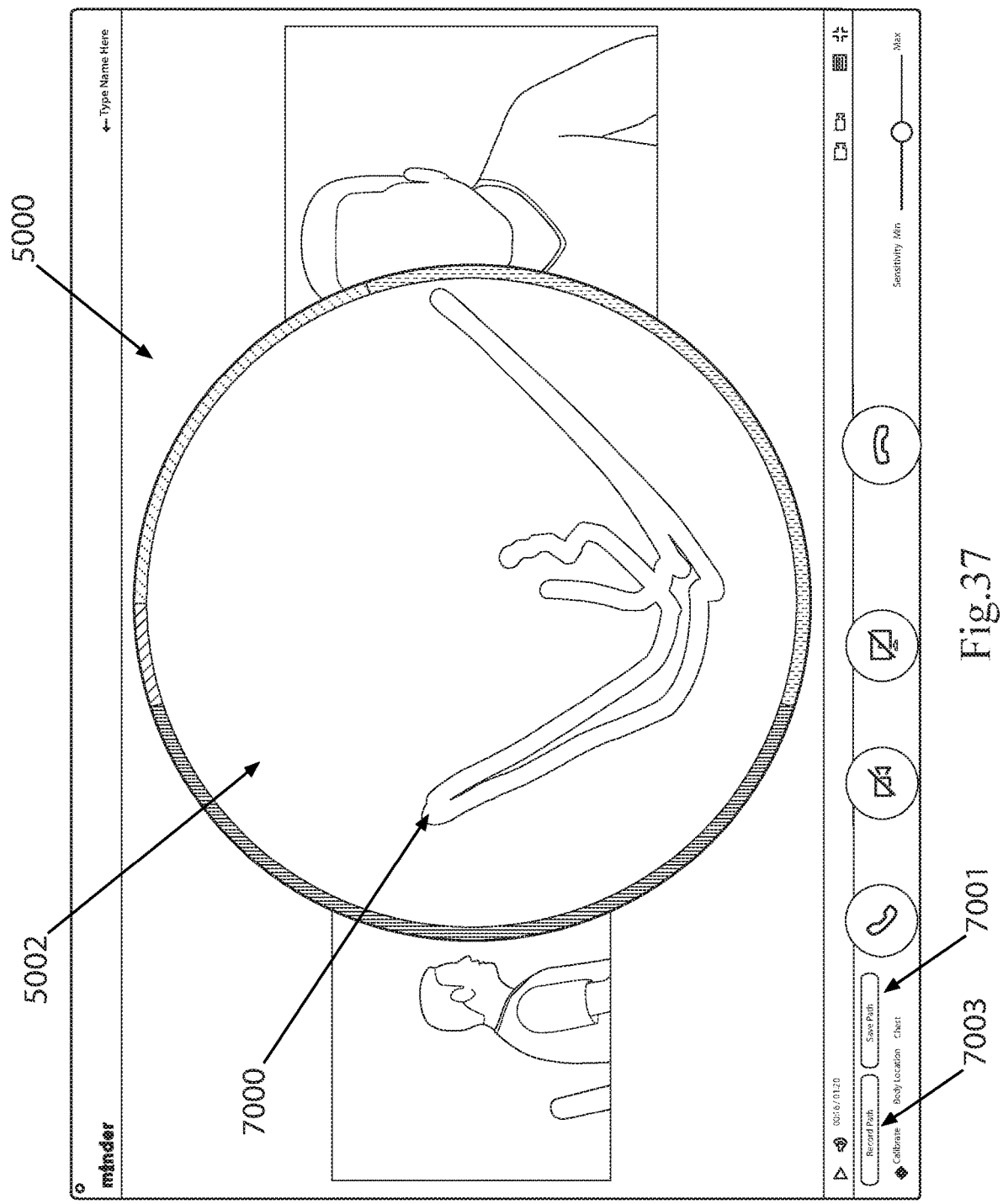

FIG. 37 is an illustration of another embodiment of the posture and deep breathing improvement system interface and shows a record of the ball path that was recorded while the user performed an exercise, which if a good exemplar may be saved as an ideal.

Figure 38:
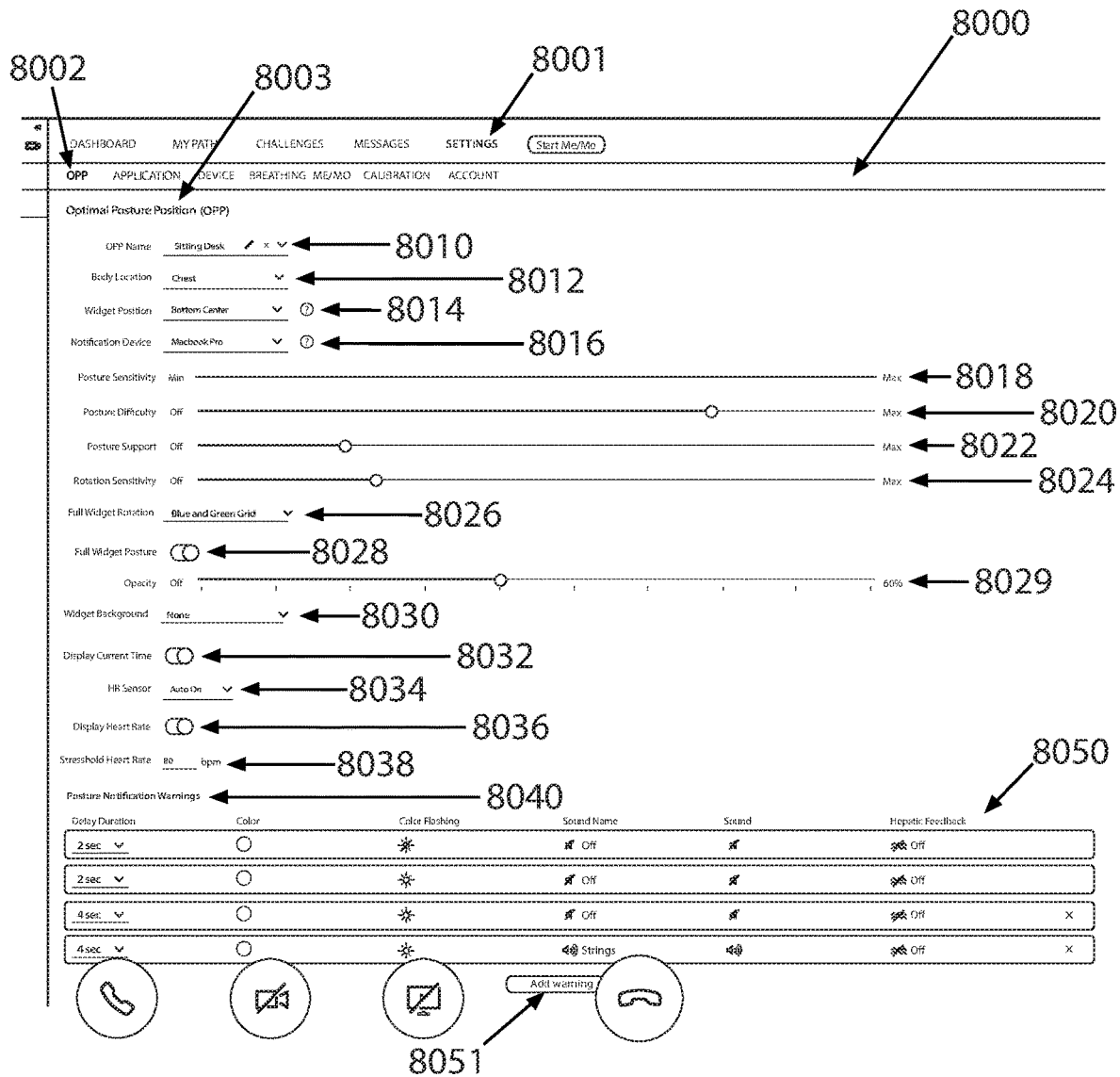

FIG. 38 is an illustration of another embodiment of the posture and deep breathing improvement system interface and shows the OPP settings screen.

DETAILED DESCRIPTION OF THE ILLUSTRATIVE EMBODIMENTS

In the following detailed description, numerous specific details are set forth in order to provide a thorough understanding of various aspects of one or more embodiments. However, the one or more embodiments may be practiced without some or all of these specific details. In other instances, well-known procedures and/or components have not been described in detail so as not to unnecessarily obscure aspects of the embodiments.

While some embodiments are disclosed herein, still other embodiments will become obvious to those skilled in the art as a result of the following detailed description. These embodiments are capable of modifications of various obvious aspects, all without departing from the spirit and scope of protection. The Figures, and their detailed descriptions, are to be regarded as illustrative in nature and not restrictive. Also, the reference or non-reference to a particular embodiment shall not be interpreted to limit the scope of protection.

DEFINITIONS

In the following description, certain terminology is used to describe certain features of one or more embodiments. For example, as used herein, the terms "computer", "computing device", or "computer system" refer to any device or machine that processes data or information with an integrated circuit chip, including without limitation, personal computers, mainframe computers, workstations, testing equipment, servers, desktop computers, portable computers, laptop computers, embedded computers, wireless devices including cellular phones, personal digital assistants, tablets, tablet computers, smartphones, portable game players, and hand-held computers. Computing devices may also include mobile computing devices such as smartphones, tablets, wearables, and the like.

As used herein, the term "Internet" generally refers to any collection of networks that utilizes standard protocols, whether Ethernet, Token ring, Wi-Fi, asynchronous transfer mode (ATM), Fiber Distributed Data Interface (FDDI), code division multiple access (CDMA), global systems for mobile communications (GSM), long term evolution (LTE), or any combination thereof. The term "website" refers to any document written in a mark-up language including, but not limited to, hypertext mark-up language (HTML) or virtual reality modeling language (VRML), dynamic HTML, extended mark-up language (XML), wireless markup language (WML), or any other computer languages related thereto, as well as to any collection of such documents reachable through one specific Internet Protocol Address or at one specific World Wide Web site, or any document obtainable through any particular Uniform Resource Locator (URL).

The terms "application", "software", "software application", or "posture improvement software program" generally refer to any set of machine-readable instructions on a client machine, web interface, and/or computer system, that directs a computer's processor to perform specific steps, processes, or operations disclosed herein. The "application", "software", "software application", and "posture improvement software program" may comprise one or more modules that direct the operation of the computing device or computer system for monitoring a conformance of the user with one or more optimum postural positions. For purposes of this specification, a module may be implemented as a hardware circuit comprising custom VLSI circuits or gate arrays, off-the-shelf semiconductors such as logic chips, transistors, or other discrete components. A module may also be implemented in programmable hardware devices such as field programmable arrays, programmable array logic, programmable logic devices, and the like. Modules may also be implemented in software for execution by various types of processors. An identified module of executable code may, for instance, comprise one or more physical or logical blocks of computer instructions, which may, for instance, be organized as an object procedure, or function. Nevertheless, the executables of an identified module need not be physically located together, but may comprise disparate instructions stored in different locations, which when joined logically together, may comprise the module and achieve the stated purpose for the module.

As used herein, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", refer to a deviance of between 0.0001-10% from the indicated number or range of numbers.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present disclosure.

Figure 1:
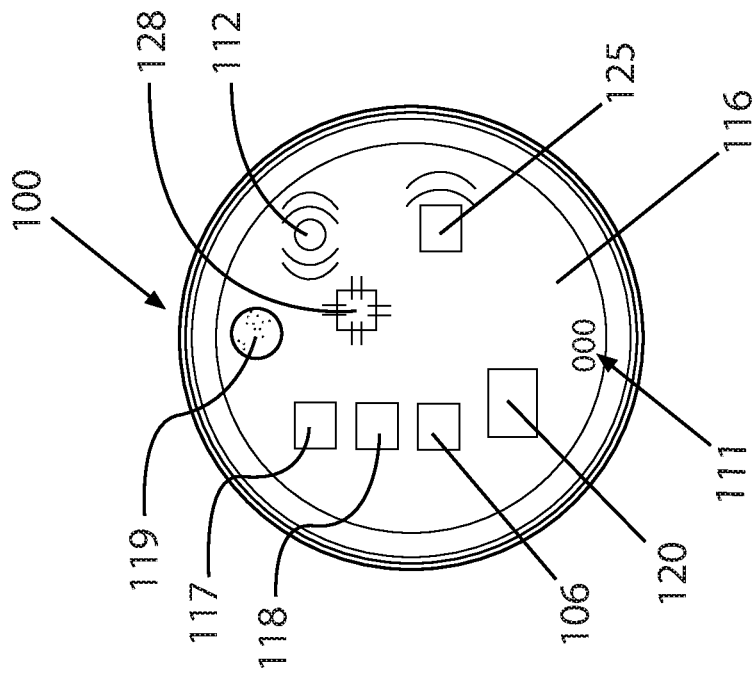
FIG. 1 is an illustration of a front view of one embodiment of the sensor device for improving posture and deep breathing.

FIG. 1 is an illustration of a front view of one embodiment of the sensor device for improving posture and deep breathing. As shown in FIG. 1, one embodiment of the sensor device 100 for improving posture may be device, wearable or otherwise positionable on a user, such that the device may be adapted to be worn or connected to the body of the user. The device 100 may comprise: a housing 116, one or more sensors 106, 117, 118, microphone 119, LED lights 111, speaker 112, power supply 120, a wireless connection device 125, and a memory unit 128.

The sensors 106, 117, 118 may comprise one or more axis-related accelerometers and one or more axis-related gyroscopes. The axis-related accelerometers may be primary sensors configured to measure slower movements of the user. The axis-related gyroscopes may be sensors configured to measure quick or exaggerated changes in the position of the user. Additionally, in other embodiments, the sensors 106, 117, 118 may further comprise a pedometer, magnometer, thermometer, respiration rate meter, heart rate meter, blood pressure meter, light level meter, and/or global positioning system. In one embodiment, the accelerometers and gyroscopes may be configured to function as a pedometer, which may inform the system that the user is walking and amount of distance traveled.

The magnometer may be configured to detect the orientation of the user, the thermometer may be configured to determine both the ambient temperature and body temperature of the user, and the global positioning system may be configured to determine the physical location of the user. When multiple types of sensors are used, information gathered by the sensors may help determine multiple characteristics of the user such as his or her weight, height, pressure, orientation, heart rate, blood pressure, and respiration rate. The sensors 106, 117, 118 may allow the system to detect any movement by the user, including breathing, deep breathing, forward, back, and/or side tilts, twisting, turning, bending, head position, and body alignment.

In a preferred embodiment, the device 100 may have three tri-axial accelerometers and three tri-axial gyroscopes. Preferably, all six sensors may be used for calibration of the system, setting the optimum postural positions (OPP) of the user, and monitoring user adherence to the OPP.

Preferably, the device 100 communicates and interfaces with an electronic data processing unit, sometimes referred to as user devices, in order for the data generated by the sensors 106, 117, 118 to be displayed to the user in an efficient and user-friendly manner.

In one embodiment, the device 100 may communicate with the user devices via a low power point-to-point communication protocol such as Bluetooth®. In other embodiments, the device may also communicate via other various protocols and technologies such as WiFi®, WiMax®, iBeacon®, near field communication (NFC) protocol, and Miracast®. In other embodiments, the device 100 may connect in a wired manner to the user devices. The wireless connection device 125 may be a transmitter, receiver, and or transceiver that communicates in any wireless manner with another electronic device.

The power supply 120 may be a battery. In various embodiments, however, the power supply 120 may also comprise an additional power source, such as alternating current electrically coupled to the sensor device 100.

The memory unit 128 may be used to capture or store data when the device 100 is not connected to a user device. In this manner, the data may be later transmitted and displayed to the user, including whether the user was able maintain his/her OPP. The sensor device or user device may each house memory and process data.

In addition to sensors 106, 117, 118, the device may also have the speaker 112, which may sound an audible alarm if the user remains out of OPP for too long, or to provide other alerts and communicative chirps to the user. The microphone 119 may act as another sensor that may be used, for example, to determine if the user is properly breathing or to intake verbal commands. The lights 111, which are preferably LED, but may be LCD or other forms of illumination, may provide the user with visual alerts or the status of the power supply (charging, needs to be charged, on, off, etc.).

Although FIG. 1 shows that the device 100 may be round or disc-shaped, the device 100 may be any shape.

Figure 3:
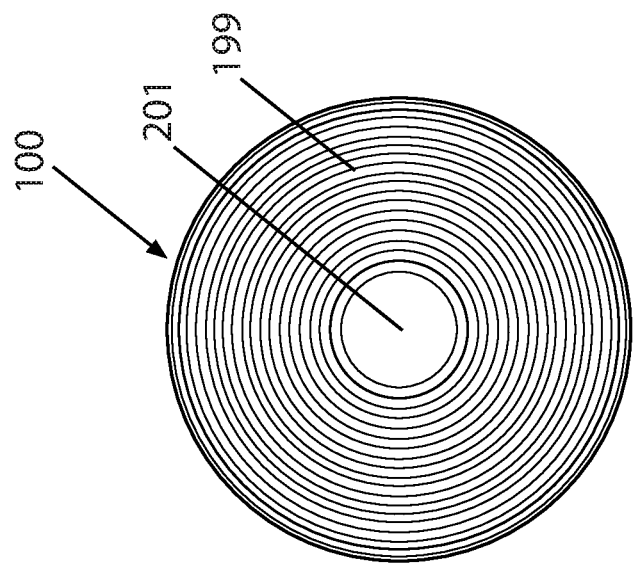
FIG. 3 is an illustration of a rear view of one embodiment of the sensor device.
Figure 2:
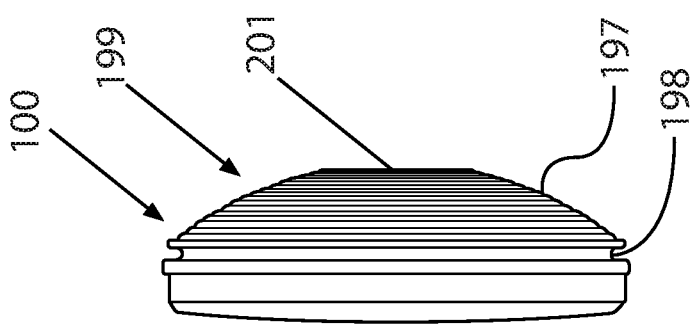
FIG. 2 is an illustration of a side view of one embodiment of the sensor device.

FIG. 2 is an illustration of a side view of one embodiment of the sensor device. FIG. 3 is an illustration of a rear view of one embodiment of the sensor device. As shown in FIGS. 2 and 3, the device 100, or more particularly, the housing the device 100, may have a concave slope 199, a connection groove 198, a copper coil 197, and a flat end 201. The copper coil 197 may allow the user to charge the power supply by touchless induction or indirect conduction. In this manner, the device 100 may not need to feature a plug or a receptacle to attach to a charging cord. The device 100 may be placed on a charging cradle and the copper coil 197 allows the device 100 to charge the power supply 120. The copper coil 197, which may be designed to face the body of a user, may also act as a shield that prevents electromagnetic radiation from passing from the device 100 to the wearer. Finally, the copper coil 197 may also direct the wireless signals away from the user and out of the front of the device 100, which may improve the wireless connection between the device and any companion or synched user devices. The flat end 201 may be at the end of the concave slope 199. The flat end 201 may be configured to rest against the body of a user. Movement of the user may cause the device 100 to roll towards the sloped side 199, which may allow the device to be very sensitive to movement, even slight movements. This sensitivity may be beneficial in determining when the user is maintaining proper balance and whether the user is breathing correctly.

FIGS. 4A-C are illustrations of one embodiment of the deep breathing and posture improvement system interface. As shown in FIG. 4A, one embodiment of the breathing and posture improvement system interface 400 may be displayed on the display screen of a user device. In this manner the user may receive real time warnings and updates from the posture and deep breathing improvement device 100. Although FIGS. 4A and 4B show the user device 100 as a LED display screen or monitor that might be part of a smart phone, laptop computer, or computer, the user device may be other computing devices, such as a smart watch, a keyboard, a mouse, eyewear, a tablet, a chair, a monitor, a smart television, or some other device that is used or worn by a user.

FIG. 4A shows that the posture and/or breathing improvement system may comprise a user device 400, which operates and displays a posture improvement system interface 420. The system interface 420 may comprise an OPP layout 425, which, as shown, may be an outline of a top plan view of a pictograph of a human. Other OPP layouts may be a bullseye, target, concentric circles, or a different pictograph, which may be relevant such as a spine that a user tries to keep in an optimum graphical shape. The system interface 420 may also comprise a posture target icon 430, which is shown as a ball, but may be any shape. For purposes of this disclosure the terms pictograph, bullseye, and target may mean the same thing. In various embodiments, the posture improvement system may be a software application running on the user device 400 that interfaces wirelessly with the device 100 in order to determine whether the user is maintaining his/her OPP. The system interface 420 may be displayed in the background or foreground of the display screen of the user device 400. When in the foreground, the system interface 420 may overlap another program. Although system interface 420 is shown as a human pictograph target 425 and posture target icon 430, it should be understood that other shapes or graphics could be used, so long as the user is provided with information regarding the maintenance of his/her OPP. FIG. 4B shows that the posture ball 430 is on the edge of the pictograph target 425, which means the user is failing to maintain the OPP. The system interface 420 may display the time 403 and the user's heart rate 402, which is preferably gathered from the device 100.

FIG. 4A also shows that the system interface 420 may comprise menus, including dashboard 605, settings 610, pause 620, and calibrate 630. When a user clicks on 430, 605, 610, 620, 630, they may expand to allow a user to interact with the system interface 420. Clicking on the ball 430 brings up the heads-up-display (HUD).

One embodiment of the system may require that the user take a periodic activity break. In one embodiment, the user is required to stretch in various directions. The target of system interface may be overlaid with a crosshair. The system may then require that the user move the posture target icon within the crosshair. This may be performed by having the user stretch to the right, back, left, and forward, which concurrently moves the posture target icon in the correct direction within the crosshair. This gamification of taking a break may prompt the user to actually comply with the request of taking an activity break. The periodic activity reminders may be set for any period, including, but not limited to, once every ten minutes, once every twenty minutes, once every thirty minutes, once an hour, and the like. In other embodiments, the user may be required to follow the icon to get to the target exercise or stretch position.

FIG. 4C is an illustration of one embodiment of the calibrate screen when the user clicks on or otherwise selects calibrate button 630. The first part of the calibration may be to have the user take some mindful breaths.

The mindful breathes may be a breathing break.

FIG. 5 is an illustration of another embodiment of the posture improvement system interface and shows pop up interface windows. As shown in FIG. 5, one embodiment of the system interface 480 may comprise an OPP layout 481, a posture target icon 482 (which, although shown as a ball or sphere, may be any shape), an instructions screen 483, a warning settings screen 485, a devices screen 483, and an OPP settings screen 487.

In one embodiment, the instructions screen 483 may be positioned to the right of the system interface 480 and may provide instructions for calibrating and using the posture system. The instructions may be provided in any form, including text, videos, graphics, flow charts, and/or pictures. The instructions screen 483 or another screen that is part of the software program may allow the user to set up and/or calibrate the posture system. Preferably, the set up and calibration may be accomplished through a decision tree or wizard that takes the user step-by-step through the process. In one embodiment, the system may prompt the user to input basic information such as his or her height and weight. The user may also input information regarding any pain the user may be experiencing. Upon receiving the information from the user, the software program may prompt the user to place the device in the proper position. In an additional embodiment, the software program may provide the user with textual, pictorial, or video instructions 483 in order to further guide the user to the proper position for the device.

The warning settings screen 485 may allow the user to set and change the warnings used by the system interface 480 for notifying the user when he/she is not in OPP. For example, in one embodiment, the user may first select the appropriate device for setting the warnings. The presentation of devices may be related to the devices screen 486. Once a device is selected, such as a phone, as shown in FIG. 5, the user may then select how the phone will warn the user of misalignment or when the user is not in his/her OPP. In various embodiments, the user may choose to be notified or warned via sound notification, change in color, flash of light or change in brightness, vibration, current or shock, other type of sensory warning, or a change in the functionality of the device. Preferably, the user sets the warnings for each device loaded in the devices screen. All warnings may be adjustable. For example, the volume of the sound warning may also be adjustable, and the brightness of the flash of light may also be adjustable. Additional colors may be selected. The strength of the vibration may be adjustable.

The devices screen 486 may allow a user to select those user devices that will communicate with the sensor device. The user devices may include, but are not limited to: a smart phone, laptop computer, a smart watch, a keyboard, a mouse, a tablet, a chair, a monitor, eyewear, a smart television, or some other device that is used or worn by a user. In some embodiments, there is no real-time user device, and the warnings are provided directly by the sensor device. In this manner, the sensor device may directly warn the user via sound, light, touch (poke), vibration, and/or click. The sensor device may include an integrated additional device that provides such a warning, or one of the existing portions of the sensor device may provide the warning.

The OPP settings screen 487 may allow the user to select one or more positions to associate with an OPP. The positions are various seated, standing, and active positions, including, but are not limited to: watching media (including, but not limited to, phone, tablet, television, and virtual reality imaging); sport/activity (including, but not limited to, walking, running, cycling, golf, baseball, basketball, yoga, snowboarding, skiing, and football); driving; working, including, but not limited to, telephone, computer, and stand up desk); hospital bed/bed ridden; travel (airplane travel); interactive games (computer and board games); presentations; personal confidence; repetitive occupational motion; specific occupational needs. Once the OPP settings are inputted into the system, the user may then calibrate each of the OPP by donning the sensor device and assuming the approximate correct position.

Once the posture improvement system is calibrated and set up, the user may use the system to ensure that the OPP is maintained during use. This is done by activating and donning the sensor device. The user must also select a user device and open the system interface 480 on that device. The system interface 480 may then inform the user whether his/her OPP is being maintained.

In one embodiment, the system interface 480 may alert the user to take periodic activity breaks, such as standing and/or stretching. The system interface 480 may also suggest a particular activity for the user to engage in during the activity break based on information regarding user pain and user conformance to his/her OPP.

Preferably, the user may switch from one OPP to another. This switch may be manually inputted by the user, thereby informing the system of the change. The switch may also be automatic, such that the device determines that the user has switched positions and intuitively changes to the more correct and appropriate OPP. This automatic switch preferably allows the user to confirm or reject the automatic switch. Regarding the automatic switch, in one embodiment, the system includes: a sensor device; and a posture improvement software program installed on multiple user devices, which possesses a notification system of OPP and an OPP display. This embodiment highlights the need for a smart and seamless network recognition system of the multiple user devices, such that the user is notified only on the appropriate user device. The description of "appropriate user device" in this embodiment is described by: proximity to other user devices, level and or the activity of the user, and user devices in use. In one example, where the seamless networking recognition system utilizes proximity as the primary factor for user device selection, a user working at a computer will have the posture improvement software displayed on the computer screen. Once the user discontinues work and leaves the proximity of the computer, the posture improvement software may no longer be required to be running on the computer. The sensor device seamlessly transitions the posture improvement software system to display on the next appropriate user device. This user device may be a smart phone, a tablet computer, a smart watch, other wearable devices, or other suitable device for OPP notification display or activity. Furthermore, the sensor device or the user device may relay information regarding active use of specific user devices as a mechanism for seamless network sensing (i.e. proximity to a computer workstation and/or the user is engaged in active use of a smart phone for an extended period, therefore, the posture improvement software displays on the smart phone). In another example, where a user chooses to engage in exercise by running, the activity level and pattern of movement detected by the sensor device will select a smart watch as the most appropriate user device, as opposed to a smart phone. In addition to these examples, a hybrid model that utilizes both proximity and activity may also be used to determine the appropriate device in which to activate the interface. In various embodiments, seamless switching between devices may be performed either automatically by the sensor, or manually selected by the user. In addition, seamless switching determination may be performed by the sensor device, or the user devices.

In various embodiments, the one or more accelerometers sense and determine the posture of the user, determine when the user takes a step, when a user takes a breath, and whether the breath is diaphragmatic. The gyroscope contributes data to the determination of the posture of the user, detecting twisting movements, and the determination as to whether the breath is diaphragmatic. In some embodiments, the user may manually set on the device or system where on the body the device will be worn (front, back, belly, neck, etc.). In other embodiments, the system may be programed to automatically detect and determine where on the body the device is placed and, if the device is moved to a different body part, the device may determine this and switch its functionality to working with the new placement on the body. In some embodiments, the heart rate monitor may be turned off or the system may remove it from the display. Turning it off may allow the battery in the device to work longer. The thermometer may display in Celsius, Fahrenheit, or both.

FIGS. 6A-C are illustrations of one embodiment of the posture and deep breathing improvement system interface. FIGS. 6A-C shows the breathing kinetic graphical user interface 500 that may be shown on the display of the user device. The interface 500 may comprise a kinetic display 510, which may comprise optimal breath inhale graphic 515 and actual dynamic kinetic breathing graphic 520, 521, 522. FIG. 6A shows that the user has inhaled a diaphragmatic breath, which is mirrored on the display 510 as the actual dynamic kinetic breathing graphic 520 expanded to at or approximately at the optimal breath inhale graphic. FIG. 6B shows that the user is exhaling in a diaphragmatic breath, which is shown by the actual dynamic kinetic breathing graphic 521 contracting 530. FIG. 6C shows that the user is inhaling in a diaphragmatic breath, which is shown by the actual dynamic kinetic breathing graphic 522 expanding 535. The breathing interface preferably allows a user to monitor his/her diaphragmatic breathing by watching the actual dynamic kinetic breathing graphic 520, 521, 522 expand and contract. The expansion of the actual dynamic kinetic breathing graphic 520, 521, 522 may optimally peak at the optimal breath inhale graphic 515, which is set by the system or the user. Although the actual dynamic kinetic breathing graphic 520, 521, 522 and the optimal breath inhale graphic 515 are shown as a circle and a dilating (telescopically expanding and contracting) dot (or ball), any kinetic graphical user interface or display may be used, so long as it translates the user's actual diaphragmatic breaths to a dynamic display that is visible to the user. In some embodiments, the kinetic breathing graphics may be shown as three-dimensional objects, such as spheres or dynamic kinetic sculptures.

The display 510 may also comprise an exhale graphic, which may be a circle that is smaller in diameter than the optimal breath inhale graphic 515 or it may be the disappearance (contracting into nothing) of the actual dynamic kinetic breathing graphic 520, 521, 522.

When the user is able to track his/her diaphragmatic breathing, the user is trained to take the optimal diaphragmatic breaths, which may significantly improve the physical and mental health of the user.

FIG. 7 is an illustration of another embodiment of the posture and deep breathing improvement system interface. As shown in FIG. 7, the interface 650 may comprise an ideal breath guide ring 651, which dilates in and out and acts as an ideal guide to the actual user breath ball 652, which is a depiction of the user's actual breathing as measured by the device. In this embodiment the user may be guided to make an ideal breath, inhale and exhale, or multiple ideal breaths.

FIG. 8 is an illustration of another embodiment of the posture and deep breathing improvement system interface. As shown in FIG. 8, the interface 660 may comprise an ideal breath guide ring 661, which dilates in and out and acts as an ideal guide to the actual user breath ball 662, which is a depiction of the user's actual breathing as measured by the device. In this embodiment the user may be guided to make an ideal breath, inhale and exhale, or multiple ideal breaths. The interface 660 may also comprise breath instructions 665, current heart rate 664, time left in the breathing session 667, and session graphic 669, which shows the number of cycles in the session and how many sessions have been completed. Session progress graphic 669 shows that the first of three sessions have been completed. FIG. 8 also shows that the interface may have a cycle time meter 670 that may comprise inhale 671, hold 672, exhale 673, and hold 674. The interface 660 may lead the user through a series of optimal deep breaths, which provides timing information 667, dynamic kinetic display 661, 662, cycle meter 670, and session progress 669.

FIG. 9 is an illustration of another embodiment of the posture and deep breathing improvement system interface and shows the settings screen. As shown in FIG. 9, when the user clicks on or otherwise selects the setting button 903 on interface 900, the user has may be presented with options, including mute/unmute 908, vibrate/no vibrate 906, quick settings 910, and OPP setting 904.

FIG. 10 is an illustration of another embodiment of the posture and deep breathing improvement system interface and shows the pause screen. When the user clicks on the pause icon or button 1001 of interface 1000, the system may pause. When the system is paused, the pause icon 1001 may become a play icon 1001, which when clicked, may start the system.

FIG. 11 is an illustration of another embodiment of the posture and deep breathing improvement system interface and shows the dashboard screen. When the user selects dashboard icon 605 on interface 400, dashboard 1100 may be pulled up. As shown in FIG. 11, the dashboard may comprise detailed information about the use of the sensor device and is a way the user may track their progress. The dashboard 1100 may have summary displays and various widgets that provide the user with information and graphs via a graphical user interface. The dashboard 1100 may comprise summary display 1101, which may comprise a greeting, rewards (Pats), user profile/avatar, wear time, weight graphic, heart rate tracking, active time, step count, percentage of time spent in OPP (good posture), Me/Mo, and the OPP interface. The dashboard 1100 may also comprise progress tracking 1102, posture report 1103, Me Moment (Me/Mo) details 1104, heart rate 1105, steps 1106, new messages 1110, input interface 1112 (which may allow the user to input data, such as body weight, mass, or body mass index), current challenge 1114, breath challenge 1116, link to view more challenges 1117, and dashboard tabs 1199.

FIG. 12 is an illustration of another embodiment of the posture and deep breathing improvement system interface and shows the HUD screen. When the user clicks on the posture ball 1430 of interface 1399, the HUD will pop up, which may comprise wear time 1440, steps 1441, posture report 1442, weight 1443, rewards 1444, temperature 1445, Me/Mo 1446, and user status 1447 (which may be shown as an emoji). When the user releases the click, or re-clicks, on the ball 1430, the HUD may retract or go away. The rewards 1444 allow users to compete against themselves and others in improving their posture, stretching, and deep breathing. This gamification of the system makes it more fun for the users and, thus, more likely that the user will participate.

FIG. 13 is an illustration of another embodiment of the posture and deep breathing improvement system interface and shows the Me/Mo screen 1650. The Me/Mo screen 1650 may pop-up and suggest that user take a personal moment for a stretch break or a breathing break 1651. The user may start this by clicking on start 1652. As shown in FIG. 11, the Me/Mo moments may be measured and tracked. The pop-up reminders may be on a set schedule, a somewhat random set schedule, or entirely random.

The pop-up reminders appearing on the interface, such as though shown in FIGS. 13 and 4C, may suggest or require action from the user, such as standing, taking a break, breathing, stretching, vocalizing, bending, walking, drinking water, performing an activity, walking the dog, feeding the cat, taking medicine, walking in place, climbing any nearby stairs, and the like. They can be custom inputted by the user or selected from a list of activities. The breathing break reminder may be a reminder to take mindful breaths.

FIG. 14 is an illustration of another embodiment of the posture and deep breathing improvement system interface and shows the dashboard settings screen. As shown in FIG. 14, the user may select settings in the dashboard tab 1199, which pulls up the OPP settings 1150 and the devices/device locations 1151. The dashboard summary 1101 may remain on the dashboard display 1100. This may allow the user to manually set the OPP (walking, sitting, standing, working, driving, playing, piano, and the like).

FIG. 15 is an illustration of one embodiment of a holder and harness for the sensor device. FIG. 15 shows that the device 100 may be configured to be cradled by holder 635 at the side groove 198 of device 100. Holder 635 may be configured to permanently or removeably hold the posture and breathing device 100. The holder 635 may be connected, permanently or removeably to a harness 610, which may be configured to be worn by a user. The harness 610 preferably may hold the device 100 next to the user in one of several specific placements so as to detect and determine the user's posture, breathing, heart rate, etc. The holder 635 and harness 610 may be connected by a hinge, such as a ball and socket, that allows free range of motion of the holder 635. The harness 610 may be rigid, flexible, fixed, adjustable, or poseable, so long as it places and generally holds in place the device in proper proximity to the user.

When the harness and holder is used to hold the device in the proper position, the device may sense and measure almost any movement of the user, including head tilting, bending, twisting, turning, standing, sitting, walking, riding, biking, running, and stretching. Preferably, the harness may be bendable, flexible, and/or, as preferred, poseable. In this manner, the user can contour the harness to his/her body structure for comfort and for maintaining the device in substantially the same place during use. In a preferred embodiment, the harness may be configured to maximize user comfort. The harness may comprise a comfortable plastic coating that houses a poseable and conforming wire (or many wires laid/wrapped/twisted in sequence) constructed of a shape-memory alloy. Shape-memory alloys, such as nickel titanium (NiTi), are also commonly referred to as SMA, smart metal, memory metal, memory alloy, muscle wire, or smart alloy. In this manner, the harness may be heated or electrically charged, put into a specific shape and then cooled or removed from the charge, such that the harness then holds this specific shape. Preferably, the device may be held in many different locations on the wearer.

FIG. 16 is an illustration of another embodiment of a holder for the sensor device. As shown in FIG. 16, one embodiment of the holder 700 may comprise a ring 710, mating protrusion 720, and connector 730. The ring 710 and mating protrusion 720 may be configured to matingly engage with a posture and breathing device, such that the posture and breathing device is held firmly and with the proper orientation by the holder 700.

FIG. 17 is an illustration of one embodiment of a poseable harness. The poseable harness 1500 may comprise a back portion 1504, front portion 1503, shoulder portion 1502, and ear buds (headphones) 1501. The poseable harness 1500 is configured to matingly and snuggly fit on the shoulders of the user in a comforting and soothing manner. The sensor device may be connected to the harness 1500 at the back dip 1505. FIG. 17 shows that the poseable harness 1500 may be constructed of a sheathed copper coil that provides additional copper related benefits to the user.

FIG. 18 is an illustration of one embodiment of a poseable harness showing retractable headphones. FIG. 18 shows that the user 1599 may don the harness 1600, which is shown without its sheath, in a manner that matingly conforms to the user's shoulders. The harness 1600 may have earbuds or headphones 1601, which have a retraction device 1602, which allows the earbuds to be used and then retractably put away. This allows the user to make dual use of the harness 1600: holding the sensor device appropriately and listening to audio entertainment.

FIG. 19 is an illustration of another embodiment of the posture and deep breathing improvement system interface and shows the settings screen. FIG. 19 shows that the settings screen 2000 of the system interface 1999 may comprise a summary display 2001, which may comprise a greeting, rewards (Pats), user profile/avatar, wear time, weight graphic, heart rate tracking, active time, step count, percentage of time spent in OPP (good posture), Me/Mo, and the OPP interface 2010. The settings screen may also comprise an interactive OPP settings portion 2200. Interactive OPP settings portion 2200 may comprise an adjustable Rotation sensitivity (from Off to Max), Full Widget rotation (with a drop down menu), Full Widget Posture (on/off switch), Transparency/Opacity (sliding scale 0 to 100%), Widget Background (drop down menu), Display Current Time (on/off switch), HR Heart Rate Sensor (drop down menu), Display Heart Rate (on/off switch), OPP Target Heart Rate (short text field followed by "bpm"), and a Posture Notification warnings section (which allows setting times, setting sounds, setting flashes, setting haptic feedback, and setting color notifications.

FIG. 20 is an illustration of another embodiment of the posture and deep breathing improvement system interface and shows the display may always be positioned in a screen foreground, regardless of what other programs are running on the computer. FIG. 20 shows that the OPP interface 3003 may always be positioned in a foreground on screen 3000 regardless of what programs are running on the user device or computer. The OPP interface 3003 may preferably have an adjustable transparency/opacity level. A transparent OPP interface 3003, as shown, allows the user to still be able to view the programs running under the OPP interface 3003.

FIG. 21 is an illustration of another embodiment of the posture and deep breathing improvement system interface and shows the activity library screen. FIG. 21 shows that the activity library screen 4001 of the system interface 4100 may comprise a summary display 4102, which may comprise a greeting, rewards (Pats), user profile/avatar, a current posture heads-up display (OPP interface), which includes the current date and time, wear time, weight graphic, heart rate tracking, body temperature reading, percentage of time spent in OPP (good posture), Me/Mo completions graphic, and the step goal. Preferably, all screens of the system interface 4100 may have a Start Me/Mo selection option 4002. Activity library screen 4001 may be accessed by selecting MY PATH from the main menu 4103 and ACTIVITIES from the sub menu 4105. The system may display ACTIVITY LIBRARY as a header 4107. The system may have a search box and execution button 4110, which may allow the user to search 4108 for specific activities already loaded into the activity library. FIG. 21 shows that there are ten activities 4120 that have been loaded into the activity library, and they may include breathing exercises (advanced, intermediate, and/or beginner), heart rate variability tests, exercise challenges, meditation exercises, mindfulness, posture exercises, nutritional exercise, strength exercises, specific condition exercises (back pain, knee pain, and the like), specific body part exercises (legs, shoulders, back, and the like), step exercises, cardio exercises, elliptical, basketball, hiking, calmness, focusing exercises, energizing, stretching exercises, and the like. The activity library screen 4001 may list the activity duration 4125. The activity library screen 4001 may inform the user how many activities are accessible 4106 and the activities may be sorted by date added, as shown, or by, for example activity type and/or activity name. The selection boxes 4126 allow a user to select one or more of the activity programs in order to tag those programs to a specific user, which allows a full program to be created. The user may delete the program by selecting boxes 4127. The user may create an activity by selecting Create Activity 4130. The user may edit the activities 4120 by selecting Edit 4140. The user may immediately start one of the listed activities 4120 by selecting Do It 4141.

Preferably, the user may select two or more activities 4120, by using 4126, which preferably allows the user to perform, simultaneously, two or more activities as Me/Mos. For example, the user may select one breathing activity (exercise or challenge) and one stretching activity (exercise or challenge), and then perform the activities simultaneously. The simultaneous activities may be done using more than one posture and breathing device of the present disclosure and using one or more external cameras.

In one embodiment, if the user selects one stretching activity and one breathing activity, the user may be required to, simultaneously, follow the ball in the stretch activity and follow the inhale, hold, exhale breathing cadence of the breath activity. The one or more cameras may allow (1) a user to record and view, (2) a user to view contemporaneous to the exercises, and/or (3) a trainer to view the user. In this manner, the user may get useful feedback on improving posture and deep breathing techniques, other than the feedback provided by the OPP interface.

In another embodiment, the activity selected by the user may have a movement component and a breathing component that allow a user to simultaneously and in synchronicity perform the movement and breathing activity. In this manner the user can perform a deep breathing exercise and a movement exercise at the same time while getting real-time feedback about the movement, visual pacing assistance for the breathing, and/or a movement guideline target to follow along to.

FIG. 22 is an illustration of another embodiment of the posture and deep breathing improvement system interface and shows the dual camera real time activity tracking screen. As shown in FIG. 22, the activity system interface 4200 may display to the user an activity tracker 4202 and two video images 4205, 4210. The video image 4210, as shown, may be an image of the user from the front, possibly from the user's web enable computer camera. The video image 4205, as shown, may be placed at a side of the user to give a side perspective. To start the one, two, or more activities, the user may select START.

FIG. 23 is an illustration of another embodiment of the posture and deep breathing improvement system interface and shows the dual camera real time activity tracking screen with an ongoing activity being tracked by cameras and the device(s). As shown in FIG. 23, the activity system interface 4200 may display to the user an activity tracker 4202 and two video images 4205, 4210. The video image 4210, as shown, may be an image of the user from the front, possibly from the user's web enable computer camera. The video image 4205, as shown, may be placed at a side of the user to give a side perspective. FIG. 23 shows that the user is performing an arms overhead stretching exercise that has been loaded into the system as an activity. The user is attempting to maintain the optimal posture position during the activity by following the moving target 4260. The moving target 4260 is following an optimal path that is set by the user or the system. The user's motion is shown as target shadow 4261. The tracker 4202 may have a timer 4203, which may be a countdown clock, so the user knows how much time has passed or is remaining in the exercise. In some embodiments, the user may also be simultaneously be doing a breathing exercise, which may be tracked and displayed on rim 4204. The activity system interface 4200 may display the name of the activities/exercise(s) being performed 4251 and may display a brand 4250.

FIG. 24 is an illustration of another embodiment of the posture and deep breathing improvement system interface and shows the result screen showing qualitative results. FIG. 24 shows the activity tracker 4202 after the activity(ies) care completed. The user may be informed that there are zero seconds left and that the activity was completed with an 87% (qualitative) accuracy 4300. The activity tracker 4202 may display the ideal path 4302 and the most recent actual path 4304. Finally, the user may be encouraged 4305. The quantitative results may be shown to the user by their performance over time.

FIG. 25 is an illustration of another embodiment of the posture and deep breathing improvement system interface and shows the real time activity tracking screen with the user using and wearing two devices. FIG. 25 shows an activity or tracking screen 4400 that shows that the user may wear two devices, the first on a neck/torso 4415 and the second on a wrist 4413. The devices 4415 and 4413 may be displayed on the body graphic 4410. Screen 4400 may be a specific follow the ball activity or track the activity (shown as 4-7-8 Breathing, which may be a program created by a user) 4403, which may be one of several grouped programs (shown as Progressive Relaxation) 4402. The screen 4400 may display the movement (or follow the ball movement) in one or more views 4420, 4430, 4440, such as top view 4420, side view 4430, and/or front view 4440. These views are created by an algorithm or software program that translates the movements detected by the sensor devices. In this manner, the user can watch and record 4460, the movements of both devices 4415, 4413. The movements may be displayed via a trailing ball (neck/torso 4421, 4431, 4441) (wrist 4422, 4432, 4442) or a follow the ball exercise. FIG. 25 also shows that the user my adjust, in real time the sensitivity 4450 of the two devices. This allows beginners to see good results and for experienced users to be challenged.

FIG. 26 is an illustration of another embodiment of the posture and deep breathing improvement system interface and shows the Start A Me/Mo pop-up, which displays a list of Me/Mos (which are exercises or tasks) that have been created and may be selected. FIG. 26 shows the interface 4500 and the app 4502 both being displayed on a computer display. The user has selected "Start a Me/Mo", which brings up the Start a Me/Mo selection list. As shown, the user may select from descriptively named exercises, such as "4-7-8 Breath (Beginner)". Preferably, the 4 is inhale, the 7 is hold, and the 8 is exhale and the duration is in seconds. As part of the gamification of the exercises the user may create many different types of exercises, some easy, some hard. The user can make the exercise more difficult by setting the sensitivity of the system to be higher. This forces the user to be more precise in his/her movements in order to accurately complete the exercises. Any combination of inhale, hold, and exhale may be used, such as 5, 5, 6.

FIG. 27 is an illustration of another embodiment of the posture and deep breathing improvement system interface and shows the Edit Your Exercise Screen. FIG. 27 shows that the Edit Your Exercise screen 4601 of the system interface 4600 may comprise a summary display 4602. The edit screen 4601 may be a result of the user selecting settings 4602 and sub-setting 4610, breathing ME/MO 4603. The user may first set the sound, sensitivity, and ring display 4620. The sound may be one of several ambient sounds that may be transmitted during the breathing exercise. These sounds are preferably white noise or other relaxing nature sounds to assist the user in relaxing during the exercise. The sensitivity may range from less to more sensitive, and the ring may be toggled on and off. The user may also edit the main breathing settings 4622. As shown, the settings may comprise number of breathing cycles, an intro sound, an inhale length, an inhale bell/sound, a hold length, a hold after inhale bell/sound, an exhale length, an exhale bell/sound, hold after exhale length, hold exhale bell/sound, and finished sound. As shown, the breathing settings 4622 may selected from drop down menus. Once the settings have been selected, the user may test it 4630, see the total time needed to complete the exercise 4632, and be provided with a breathing cycle preview 4624. The edit screen allows the user to create the desired visual and audio prompts, which causes the system to be a configurable metronome.

Being able to create and edit breathing exercises allows each individual user to create the program that is optimal for them.

FIG. 28 is an illustration of another embodiment of the posture and deep breathing improvement system interface and shows the interactive schedule screen. FIG. 28 shows that the interactive schedule screen 4700 may comprise a summary display 4702. The schedule screen 4700 may be a result of the user selecting MY PATH from the settings 4710 and SCHEDULE from the sub-setting 4712. As shown, the SCHEDULE may display a specific day 4720 and allow the user to track exercises that are completed and to schedule future exercises. The user may add exercises to the SCHEDULE by selecting ADD ME/MO 4715. The SCHEDULE may display the scheduled exercises 4730. After the user completes an exercise, the SCHEDULE may be automatically or manually updated to show that the exercise was, in fact, completed. Exercises 4731 and 4732 were scheduled, completed, and entered as completed. Exercises 4733 and 4734 are scheduled, but not yet entered as completed. Exercises 4733 and 4734 are in red, because they are in the past, but not yet marked as completed. The SCHEDULE may also comprise additional, non-exercise tasks 4735, which include logging your weight, eating a healthy breakfast, and drinking water throughout the day. Preferably, the system may award points for each task completed and logged. This gamification is an important motivator for getting users to actually complete the exercises and other tasks.

FIG. 29 is an illustration of another embodiment of the posture and deep breathing improvement system interface and shows the interactive schedule screen. FIG. 29 shows schedule screen 4700 now with tasks/exercises 4734 and 4735 entered as completed. Task 4735 was not completed, so it stays in red. Exercises 4736 and 4737 are in the future so are in blue.

FIG. 30 is an illustration of another embodiment of the posture and deep breathing improvement system interface and shows the create an activity screen. FIG. 30 shows that the user selects MY PATH 4810 and ACTIVITIES 4812 to get to the create an activity screen 4800 in order to edit activity 4814. The create activity screen 4800 is an interface that may comprise a CLOSE WITHOUT SAVING 4820 option, a SAVE ACTIVITY 4822 option that allows the user to exit or exit and save. The screen 4800 may comprise the entry and selection (drop down and otherwise) fields:

ACTIVITY NAME 4830—allows the user to name the activity being created/edited ACTIVITY TYPE 4831—allows the user to select one of the provided activity types AMBIENT SOUND 4832—allows the user to select the sound, if any, playing during the activity DEVICE LOCATION 4833—allows the user to select where the device will be placed on the user during the exercise (chest, neck, back, wrist, belt, ankle, etc.). If the activity will have two or more devices used, then the user may select multiple locations.

INTRO SOUND 4834—lets the user know the activity is about to start

INTRO TIMER 4835—sets the count down to when the activity will start

INTRO MESSAGE 4836—sets the message to be displayed to the user when the activity starts OUTRO SOUND 4837—lets the user know the activity is finished TOTAL ACTIVITY TIME 4838—sets how long the activity will last BREATHING PATTERN 4850—for each activity type, the user has the option of setting a breathing pattern to be followed while the activity is performed. This breathing is preferably synchronized with the activity/exercise being performed.

NUMBER OF BREATHING CYCLES 4851—sets the number of times the breathing pattern will be done INHALE LENGTH 4852—for each cycle, an inhale length is selected INHALE SOUND 4853—sets what sound/chime is played to start the inhale step HOLD AFTER INHALE LENGTH 4854—sets how long the user holds after inhaling HOLD AFTER INHALE SOUND 4855—set what sound is played to start the hold after inhale EXHALE LENGTH 4856—sets how long the user exhales after the hold after the inhale EXHALE SOUND 4857—sets what sound is played to start the exhale FIG. 31 is an illustration of another embodiment of the posture and deep breathing improvement system interface and shows the create an activity screen. FIG. 31 shows the rest of the create an activity screen may comprise:

EXHALE SOUND 4857—sets what sound is played to start the exhale

HOLD AFTER EXHALE LENGTH 4858—sets the length of the hold after the exhale

HOLD AFTER EXHALE SOUND 4859—sets the sound that starts the hold after the exhale FIG. 31 also shows that the user has an option of adding a tutorial video for the activity.

FIG. 32 is an illustration of another embodiment of the posture and deep breathing improvement system interface and shows the create an activity screen with a list of activities from which to select. As shown in FIG. 32, the user may select an activity from the list of breathing, meditation, stretching, and strength 4831.

FIG. 33 is an illustration of another embodiment of the posture and deep breathing improvement system interface and shows the create activity screen and selecting the follow the ball path option. As shown in FIG. 33, the user may set the created activity program to include a follow the ball path recording 4900. With this option, in addition to the user performing the exercise/activity, an exemplar, pre-recorded ball is provided for the user to follow along with while doing the activity. Each future time the user performs the saved activity, a resulting follow path is displayed at the end of the activity and be compared to the exemplar that is saved when creating or editing the activity.

FIG. 34 is an illustration of another embodiment of the posture and deep breathing improvement system interface and shows the create activity screen and selecting the follow the ball path option selected. FIG. 34 shows that once a user opens the follow the ball path recording 4900 selection, the user may then set the activity to record 4902 the ball path each time the activity is completed. The user may also make a recording of the exemplar ball path.

FIG. 35 is an illustration of another embodiment of the posture and deep breathing improvement system interface and shows the record the ball path start screen. FIG. 35 shows the screen 5000 that may allow the user to record an exemplar of a specific activity, such as a stretching activity. Screen 5000 shows a blank activity tracker 5002, a rim 5004, video images 5005, 5010, record button 5020, location selection display 5030, and sensitivity adjustment bar 5050. After the user hits the record button 5020, the user may then record an optimal or exemplar path, which is then used by the user as an optimal ball in which to follow when the activity is scheduled and performed later by the user. Just like when the user performs the activity later, the recordation provides the user with the same introduction timer count down and displays a message about the start of the recordation/activity, which includes recording on the cameras 5005, 5010, recording the activity on the tracker 5002. Preferably, the activity that is performed and recorded by the user is synchronized with the breathing activity that is tracked on the rim 5004. The user may set the sensitivity of the recordation 5050. If the user is an expert, the sensitivity can be set high, so that a little bit of physical movement by the user translates to a lot of movement on the screen tracker 5002. If the user is new to the system, the sensitivity may be set low so that the user does not get frustrated when doing the activity at a later scheduled time.

FIG. 36 is an illustration of another embodiment of the posture and deep breathing improvement system interface and shows the record the ball path being recorded while the user performs an exercise. After the user starts the recording 5020, the recording timer 5055 starts, the timer 5003 is displayed, the rim 5004 provides the user guidance on the selected breathing options related to the exercise. FIG. 36 shows that that the tracker 5002 shows the user's current movement 6000, in real time. If the user messes up the recording, they can simply stop recording 5021 and start over 5020. Preferably the recording of the follow the ball is an optimal or substantially optimal recording of the activity. This gives the user something to strive for each future time that activity is on the user's schedule.

FIG. 37 is an illustration of another embodiment of the posture and deep breathing improvement system interface and shows a record of the ball path that was recorded while the user performed an activity being created. FIG. 37 shows that the results of the user's tracked activity 7000 are displayed on the tracker 5002 of the screen 5000. If the tracked activity is good and the user is satisfied, then it can be saved 7001. If the user is unsatisfied with the tracked activity (which will later become a ball or target that the user follows) when doing the activity, then the user can start the recording over 7003. FIG. 24 shows an example of an activity being done later and being compared to the exemplar that was saved during a creation or editing of an activity.

FIG. 38 is an illustration of another embodiment of the posture and deep breathing improvement system interface and shows the OPP settings screen. As shown in FIG. 38, the user may set the Optimal Posture Positions, which allow the user to use the device and monitor an ongoing good posture. The user gets to the Optimal Posture Position settings screen 8000 by selecting SETTINGS 8001 and OPP 8002. FIG. 38 shows that the OPP 8003 settings options include, but are not limited to, the following entry and selection fields:

- OPP NAME—8010—allows the user to select what position is being optimized, walking, sitting, standing, laying down, running, and the like
- BODY LOCATION—8012—sets where on the body the device is placed
- WIDGET POSITION—8014—sets where the default position of where the graphical display of the program is on the user's screen
- NOTIFICATION DEVICE—8016—sets which device or devices notify the user when not in posture compliance
- POSTURE SENSITIVITY—8018—sets how sensitive the device is to user movement
- POSTURE DIFFICULTY—8020—sets how accurate the user must hold their posture in order to be in compliance
- POSTURE SUPPORT—8022—this relates to whether the user may be using a chair or a bench with backing. This allows for movement backward into the chair backing to be still within an acceptable posture, but side movement might not be acceptable. This sets an acceptable good range to lean back.
- ROTATION SENSITIVITY—8024—sets how sensitive the device is to rotational movement by the user
- FULL WIDGET ROTATION—8026—sets a background pattern behind the target. The widget rotation may preferably be tied to the gyroscope of the various sensor devices.
- FULL WIDGET POSTURE—8028—off is only full widget rotation on screen. On is with target ball.
- OPACITY—8029—sets the transparency properties of the widget
- WIDGET BACKGROUND—8030—sets the background pattern/color of the widget, if any
- DISPLAY TIME—8032—enables/disables the display of the current time
- HR SENSOR—8034—turns on/off the heart rate sensor
- DISPLAY HR HEART RATE—8036—enables/disables the display of the users heart rate on the widget
- STRESSHOLD HEART RATE—8038—this sets a heart rate alarm. If you go above the stress hold heart rate then the system provides a pop-up message to take a memo, for example.
- POSTURE NOTIFICATION WARNINGS—8040—allows the user to set what warnings they get
- WARNINGS SETTING—8050—as shown in FIG. 38, the user may set a series of warnings, in this case four (4) that may have a delay duration, a specific color (redder and darker for more out of optimum), flashing, sound warning, and whether there is any haptic feedback.

Unless otherwise stated, all measurements, values, ratings, positions, magnitudes, sizes, locations, and other specifications that are set forth in this specification, including in the claims that follow, are approximate, not exact. They are intended to have a reasonable range that is consistent with the functions to which they relate and with what is customary in the art to which they pertain.

The foregoing description of the preferred embodiment has been presented for the purposes of illustration and description. While multiple embodiments are disclosed, still other embodiments will become apparent to those skilled in the art from the above detailed description, which shows and describes the illustrative embodiments. These embodiments are capable of modifications in various obvious aspects, all without departing from the spirit and scope of protection. Accordingly, the detailed description is to be regarded as illustrative in nature and not restrictive. Also, although not explicitly recited, one or more embodiments may be practiced in combination or conjunction with one another. Furthermore, the reference or non-reference to a particular embodiment shall not be interpreted to limit the scope of protection. It is intended that the scope not be limited by this detailed description, but by the claims and the equivalents to the claims that are appended hereto.

Except as stated immediately above, nothing that has been stated or illustrated is intended or should be interpreted to cause a dedication of any component, step, feature, object, benefit, advantage, or equivalent, to the public, regardless of whether it is or is not recited in the claims.

What is claimed is:

1. A method of performing a deep breathing and posture activity, comprising:
providing two or more sensor devices;
providing a posture improvement software program, comprising a posture improvement system interface and a create an activity interface;
associating said two or more sensor devices physically with a user;
wherein each of said two or more sensor devices comprise: one or more sensors; a wireless communication device; and a housing;
wherein each of said one or more sensors, when said two or more sensor devices are physically associated with said user, monitor a physical position of said user and one or more movements of said user;

wherein said posture improvement software program is configured to operate on one or more user devices;
wherein said wireless communication device is configured to communicate with said one or more user devices, such that said two or more sensor devices are in communication with said posture improvement software program;
displaying said posture improvement system interface to said user on said one or more user devices;
creating one or more activity programs via said create an activity interface;
wherein said one or more activity programs comprise a breathing component, a movement component, and a recordation of a follow the target;
starting at least one of said one or more activity programs;
performing by said user said at least one of said one or more activity programs;
displaying to said user an activity tracker on said posture improvement system interface;
displaying on said activity tracker said recordation of a follow the target, a graphical representation of said breathing component, and a graphical representation of said movement component;
wherein said recordation of a follow the target provides said user with two or more graphical representations of two or more targets to follow as said user performs said at least one of said one or more activity programs; and
transmitting from each of said two or more sensor devices a plurality of movement data to said posture improvement software program, which is translated into said graphical representation of said movement component that is being displayed on said activity tracker, such that said user receives a plurality of real-time visual feed-back related to said user's conformance to said movement component.

2. The method of claim 1, wherein said posture improvement software program schedules said one or more activity programs to be performed by said user.

3. The method of claim 1, wherein said breathing component and said movement component are synchronized and are performed simultaneously by said user.

4. The method of claim 1, wherein each of said two or more targets are a graphical representation of a ball.

5. The method of claim 1, wherein said one or more activity programs are selected from the group of activity programs consisting of one or more of: strength; breathing; stretching; meditation; and combinations thereof.

6. The method of claim 1, wherein said breathing component comprises one or more cycles of deep breathing that comprise at least an inhale and an exhale.

7. The method of claim 1, further comprising:
displaying on said activity tracker two or more ideal paths, which are representative of two or more paths taken by said two or more targets, and two or more actual paths, which are representative of two or more paths taken by said user performing said at least one of said one or more activity programs, such that said user is provided with feed-back as to how said user did in performing said at least one of said one or more activity programs.

8. The method of claim 1, further comprising:
providing two or more video cameras that are in communication with said posture improvement software program;
displaying on said posture improvement system interface a live feed from said two or more video cameras as said user performs said at least one of said one or more activity programs.

9. A method of performing a deep breathing and posture activity, comprising:
providing a sensor device;
providing a posture improvement software program, comprising a posture improvement system interface and a create an activity interface;
associating said sensor device physically with a user;
wherein said sensor device comprises: one or more sensors; a wireless communication device; and a housing;
wherein said one or more sensors, when said sensor device is physically associated with said user, monitor a physical position of said user and one or more movements of said user;
wherein said posture improvement software program is configured to operate on one or more user devices;
wherein said wireless communication device is configured to communicate with said one or more user devices, such that said one or more sensor devices are in communication with said posture improvement software program;
displaying said posture improvement system interface to said user on said one or more user devices;
creating one or more activity programs via said create an activity interface;
wherein said one or more activity programs comprise a movement component and a recordation of a follow the target;
starting at least one of said one or more activity programs;
performing by said user said at least one of said one or more activity programs;
displaying to said user an activity tracker on said posture improvement system interface;
displaying on said activity tracker said recordation of a follow the target and a graphical representation of said movement component;
wherein said recordation of a follow the target provides said user with a graphical representation of a target to follow as said user performs said at least one of said one or more activity programs; and
transmitting from said sensor device a plurality of movement data to said posture improvement software program, which is translated into said graphical representation of said movement component that is being displayed on said activity tracker, such that said user receives a plurality of real-time visual feed-back related to said user's conformance to said movement component.

10. The method of claim 9, wherein said one or more activity programs further comprise a breathing component;
wherein said breathing component is displayed as at least one dynamic graphical representation on said activity tracker.

11. The method of claim 10, further comprising:
providing two or more video cameras that are in communication with said posture improvement software program;
displaying on said posture improvement system interface a live feed from said two or more video cameras as said user performs said at least one of said one or more activity programs.

12. The method of claim 10, wherein said posture improvement software program schedules said one or more activity programs to be performed by said user.

13. The method of claim 10, wherein said breathing component and said movement component are synchronized and are performed simultaneously by said user.

14. The method of claim 10, wherein said target is a graphical representation of a ball.

15. The method of claim 10, wherein said one or more activity programs are selected from the group of activity programs consisting of one or more of: strength; breathing; stretching; meditation; and combinations thereof.

16. The method of claim 10, wherein said breathing component comprises one or more cycles of deep breathing that comprise at least an inhale and an exhale.

17. The method of claim 16, wherein one or more portions of said one or more cycles of deep breathing are prompted by one or more sounds.

18. The method of claim 10, further comprising:
displaying on said activity tracker an ideal path, which is representative of a path taken by said target, and an actual path, which is representative of a path taken by said user performing said at least one of said one or more activity programs, such that said user is provided with feed-back as to how said user did in performing said at least one of said one or more activity programs.

19. A method of performing a deep breathing and posture activity, comprising:
providing a sensor device;
providing a posture improvement software program, comprising a posture improvement system interface and a create an activity interface;
associating said sensor device physically with a user;
providing two or more video cameras that are in communication with said posture improvement software program;
wherein said sensor device comprises: one or more sensors; a wireless communication device; and a housing;
wherein said one or more sensors, when said sensor device is physically associated with said user, monitor a physical position of said user and one or more movements of said user;
wherein said posture improvement software program is configured to operate on one or more user devices;
wherein said wireless communication device is configured to communicate with said one or more user devices, such that said one or more sensor devices are in communication with said posture improvement software program;
displaying said posture improvement system interface to said user on said one or more user devices;
creating one or more activity programs via said create an activity interface;
wherein said one or more activity programs comprise a movement component, a breathing component, and a recordation of a follow the target;
starting at least one of said one or more activity programs;
performing by said user said at least one of said one or more activity programs;
displaying to said user an activity tracker on said posture improvement system interface;
displaying on said activity tracker said recordation of a follow the target, a graphical representation of said breathing component, and a graphical representation of said movement component;
wherein said recordation of a follow the target provides said user with a graphical representation of a target to follow as said user performs said at least one of said one or more activity programs; and
transmitting from said sensor device a plurality of movement data to said posture improvement software program, which is translated into said graphical representation of said movement component that is being displayed on said activity tracker, such that said user receives a plurality of real-time visual feed-back related to said user's conformance to said movement component;
displaying on said posture improvement system interface, a live feed from said two or more video cameras as said user performs said at least one of said one or more activity programs;
displaying, after a conclusion of said at least one of said one or more activity programs, on said activity tracker, an ideal path, which is representative of a path taken by said target, and an actual path, which is representative of a path taken by said user performing said at least one of said one or more activity programs, such that said user is provided with feed-back as to how said user did in performing said at least one of said one or more activity programs.

20. The method of claim 19, wherein said breathing component and said movement component are synchronized and are performed simultaneously by said user.

21. The method of claim 19, wherein said one or more activity programs are selected from the group of activity programs consisting of one or more of: strength; breathing; stretching; meditation; and combinations thereof.

22. The method of claim 19, wherein at least one of said two or more cameras is configured to show a profile of said user.

* * * * *